United States Patent
Artieri et al.

(10) Patent No.: US 12,322,476 B2
(45) Date of Patent: Jun. 3, 2025

(54) METHODS FOR DETECTING AND SUPPRESSING ALIGNMENT ERRORS CAUSED BY FUSION EVENTS

(71) Applicant: GUARDANT HEALTH, INC., Redwood City, CA (US)

(72) Inventors: Carlo Artieri, Redwood City, CA (US); Marcin Sikora, Redwood City, CA (US)

(73) Assignee: Guardant Health, Inc., Palo Alto, CA (US)

( * ) Notice: Subject to any disclaimer, the term of this patent is extended or adjusted under 35 U.S.C. 154(b) by 1076 days.

(21) Appl. No.: 16/383,349

(22) Filed: Apr. 12, 2019

(65) Prior Publication Data

US 2020/0020416 A1  Jan. 16, 2020

Related U.S. Application Data

(60) Provisional application No. 62/657,200, filed on Apr. 13, 2018.

(51) Int. Cl.
  *G16B 20/00* (2019.01)
  *G16B 30/00* (2019.01)
  *G16B 40/00* (2019.01)
(52) U.S. Cl.
  CPC ............. *G16B 20/00* (2019.02); *G16B 30/00* (2019.02); *G16B 40/00* (2019.02)
(58) Field of Classification Search
  None
  See application file for complete search history.

(56) References Cited

U.S. PATENT DOCUMENTS

| | | | |
|---|---|---|---|
| 6,582,908 B2 | 6/2003 | Fodor et al. | |
| 7,537,898 B2 | 5/2009 | Bost et al. | |
| 9,598,731 B2 | 3/2017 | Talasaz | |
| 2001/0053519 A1 | 12/2001 | Fodor et al. | |
| 2011/0160078 A1 | 6/2011 | Fodor et al. | |
| 2014/0315199 A1 | 10/2014 | Rhodes et al. | |
| 2015/0191795 A1 | 7/2015 | Chinnaiyan et al. | |
| 2018/0251848 A1 | 9/2018 | Diehn et al. | |

FOREIGN PATENT DOCUMENTS

WO  2014172046 A2  10/2014

OTHER PUBLICATIONS

Daniel MacLean, and Jonathan D. G Jones. "Application of 'Next-Generation' Sequencing Technologies to Microbial Genetics." Nature reviews. Microbiology 7.4 (2009): 287-296. Web. (Year: 2009).*
Kinsella, Marcus et al. "Sensitive Gene Fusion Detection Using Ambiguously Mapping RNA-Seq Read Pairs." Bioinformatics 27.8 (2011): 1068-1075. Web. (Year: 2011).*
Lanman, Richard B et al. "Analytical and Clinical Validation of a Digital Sequencing Panel for Quantitative, Highly Accurate Evaluation of Cell-Free Circulating Tumor DNA." PloS one 10.10 (2015): e0140712-e0140712. Web. (Year: 2015).*
Agarwal, N., Pal, S. K., Hahn, A. W., Nussenzveig, R. H., Pond, G. R., Gupta, S. V., . . . & Grivas, P. (2018). Characterization of metastatic urothelial carcinoma via comprehensive genomic profiling of circulating tumor DNA. Cancer, 124(10), 2115-2124. (Year: 2018).*
Kohda, Masakazu et al. "Rapid Detection of Germline Mutations for Hereditary Gastrointestinal Polyposis/cancers Using HaloPlex Target Enrichment and High-Throughput Sequencing Technologies." Familial cancer 15.4 (2016): 553-562. Web. (Year: 2016).*
Cooke, S.L et al. "Processed Pseudogenes Acquired Somatically During Cancer Development." Nature communications 5.1 (2014): 3644-. Web. (Year: 2014).*
Kim, Daehwan et al. "TopHat2: Accurate Alignment of Transcriptomes in the Presence of Insertions, Deletions and Gene Fusions." Genome biology 14.4 (2013) (Year: 2013).*
Van Allen EM, Wagle N, Levy MA. Clinical analysis and interpretation of cancer genome data. J Clin Oncol. May 20, 2013;31(15):1825-33. (Year: 2013).*
Vandekerkhove G, Todenhöfer T, Annala M, Struss WJ et al . Circulating Tumor DNA Reveals Clinically Actionable Somatic Genome of Metastatic Bladder Cancer. Clin Cancer Res. Nov. 1, 2017;23(21):6487-6497 (Year: 2017).*
Shlien A, Raine K, Fuligni F, Arnold R, Nik-Zainal S, Dronov S, Mamanova L, et al . Direct Transcriptional Consequences of Somatic Mutation in Breast Cancer. Cell Rep. Aug. 16, 2016;16(7):2032-46. (Year: 2016).*
Narayan A, Carriero NJ, Gettinger SN, Kluytenaar J,et al . Ultrasensitive measurement of hotspot mutations in tumor DNA in blood using error-suppressed multiplexed deep sequencing. Cancer Res. Jul. 15, 2012;72(14):3492-8. doi: 10.1158/0008-5472.CAN-11-4037. Epub May 10, 2012. (Year: 2012).*
Huang AY, Xu X, Ye AY, Wu Q, Yan L, Zhao B, Yang X, He Y, Wang S, Zhang Z, Gu B, Zhao HQ, Wang M, Gao H, Gao G, Zhang Z, Yang X, Wu X, Zhang Y, Wei L. Postzygotic single-nucleotide mosaicisms in whole-genome sequences of clinically unremarkable individuals. Cell Res. Nov. 2014;24(11):1311-27. (Year: 2014).*

(Continued)

*Primary Examiner* — Anna Skibinsky
*Assistant Examiner* — Joseph Pulliam
(74) *Attorney, Agent, or Firm* — Timothy A. Hott

(57) ABSTRACT

Methods for producing a filtered sequencing data set by identifying one or more split sequence reads in a set of test sequence reads obtained from cell-free nucleic acid (cfNA) in a biological sample, wherein each split sequence read comprises at least one breakpoint; and, suppressing, in the set of test sequence reads, (i) at least a portion of one or more of the split sequence reads and/or at least a portion of one or more of the test sequence reads that comprise at least one sequence variant within a selected number of nucleotides from a given breakpoint, (ii) one or more base calls of the split sequence reads and/or one or more base calls of the test sequence reads that comprise at least one sequence variant within a selected number of nucleotides from a given breakpoint, thereby producing the filtered sequence information data set.

11 Claims, 7 Drawing Sheets

Specification includes a Sequence Listing.

(56) References Cited

OTHER PUBLICATIONS

Cole, A. J., Zhu, Y., Dwight, T., Yu, B., Dickson, K. A., Gard, G. B., Maidens, J., Valmadre, S., Gill, A. J., Clifton-Bligh, R., & Marsh, D. J. (2017). Comprehensive analyses of somatic TP53 mutation in tumors with variable mutant allele frequency. Scientific data, 4, 170120. (Year: 2017).*

Roy, S., Coldren, C., Karunamurthy, A . . . et al. (2018). Standards and Guidelines for Validating Next-Generation Sequencing Bioinformatics Pipelines: A Joint Recommendation of the Association for Molecular Pathology and the College of American Pathologists (Year: 2018).*

Ernani V, Ganti AK. Immunotherapy in treatment naïve advanced non-small cell lung cancer. J Thorac Dis. Feb. 2018; 10(Suppl 3): S412-S421. (Year: 2017).*

Zhao X, Wang A, Walter V,. Combined Targeted DNA Sequencing in Non-Small Cell Lung Cancer (NSCLC) Using UNCseq and NGScopy, and RNA Sequencing Using UNCqeR for the Detection of Genetic Aberrations in NSCLC. PLoS One. Jun. 15, 2015;10(6): e0129280. (Year: 2015).*

Thompson, Bryony A et al. "Application of a 5-tiered scheme for standardized classification of 2,360 unique mismatch repair gene variants in the InSIGHT locus-specific database." Nature Genetics 46.2 (2014): 107-115. Web. (Year: 2014).*

Lanman, Richard B et al. "Analytical and Clinical Validation of a Digital Sequencing Panel for Quantitative, Highly Accurate Evaluation of Cell-Free Circulating Tumor DNA." PloS one 10.10 (2015): e0140712-e0140712. Web. Supplemental Table (Year: 2016).*

Clark, T.A. et al. "Analytical Validation of a Hybrid Capture Based Next-Generation Sequencing Clinical Assay for Genomic Profiling of Cell-Free Circulating Tumor Dna," J. Mol. Diagnostics (2018) 20(5):686-702.

Cock, PJA, et al. "The Sanger FASTQ file format for sequences with quality scores, and the Solexa/Illumina FASTQ variants" NAR (2009) 38(6):1767-1771.

Cooke et al. "Processed pseudogenes acquired somatically during cancer development" Nature Commun (2014) 5:3644.

Danecek, P. et al. "The variant call format and VCFtools" Bioinformatics (2011) 27(15):2156-2158.

Esnault et al., "Human LINE retrotransposons generate processed pseudogenes" Nature Genetics (2000) 24:363-367.

International search report and written opinion dated Jul. 18, 2019 for PCT/US2019/027337.

Kim, D. et al. "TopHat2: accurate alignment of transcriptomes in the presence of insertions, deletions, and gene fusions" Genome Biology (2013) 14:R36.

Li, et al. Mapping short DNA sequencing reads and calling variants using mapping quality scores. Genome Res. Nov. 2008;18(11):1851-8. doi: 10.1101/gr.078212.108. Epub Aug. 19, 2008.

Millson et al. "Processed Pseudogene Confounding Deletion/ Duplication Assays for SMAD4" J Mol Diag (2015) 17:576-582.

Newman, et al. An ultrasensitive method for quantitating circulating tumor DNA with broad patient coverage. Nat Med. May 2014;20(5):548-54. doi: 10.1038/nm.3519. Epub Apr. 6, 2014.

Ning, Z. et al. "SSAHA: A Fast Search Method for Large DNA Databases" Genome Res (2001) 11:1725-1729.

Pardoll, D.M. "The blockade of immune checkpoints in cancer immunotherapy" Nature Rev Cancer (2012) 12:252-264.

Paweletz, C.P. et al. "Bias-corrected targeted next-generation sequencing for rapid, multiplexed detection of actionable alterations in cell-free DNA from advanced lung cancer patients" Clin Canc Res (2016) 22(4):915-922.

Pearson, W.R. et al. "Improved tools for biological sequence comparison" PNAS (1988) 85:2444-2448.

Phallen, J. et al. "Direct detection of early-stage cancers using circulating tumor DNA" Sci Trans Med (2017) vol. 9, Issue 403, eaan2415DOI: 10.1126/scitranslmed aan2415.

Extended European search report and opinion dated Dec. 2, 2021 for EP Application No. 19786130.5.

* cited by examiner

METHODS FOR DETECTING AND SUPPRESSING ALIGNMENT ERRORS CAUSED BY FUSION EVENTS

CROSS-REFERENCE

This Patent Application claims priority to U.S. Provisional Patent Application No. 62/657,200, filed on Apr. 13, 2018, which is herein incorporated by reference in its entirety.

SEQUENCE LISTING

The instant application contains a Sequence Listing which has been submitted electronically in ASCII format and is hereby incorporated by reference in its entirety. Said ASCII copy, created on Mar. 30, 2023, is named 42534-788_201_SL.txt and is 2,432 bytes in size.

BACKGROUND

Duplicated genomic regions caused by genomic rearrangement events may pose a challenge to accurate variant calling in clinical sequencing applications, as duplicate-specific variants may incorrectly be assigned to a target. Processed pseudogenes (PPGs) are a source of duplicated coding sequences that can originate from LINE (Long Interspersed Elements)-mediated reverse transcription and genomic integration of processed mRNA, resulting in partial or complete copies of the original gene, lacking intronic sequences. False-positive variants resulting from pseudogenes found in the reference genome, such as those of PIK3CA and PTEN, have been well studied; however, the discovery of rare and even individual-specific cancer-related PPGs demonstrates a need for more systematic interrogation and mediation of PPG-related clinical artefacts on a sample-by-sample basis.

SUMMARY

In certain aspects, the present disclosure provides a method for detecting alignment errors in genetic sequence reads, comprising: sequencing cell-free deoxyribonucleic acid (DNA) molecules from a sample of a subject, wherein each of the cell-free DNA molecules generates a plurality of sequence reads; aligning sequence reads derived from the sequencing to a reference sequence to produce aligned sequence reads; identifying, from the aligned sequence reads, a set of gene fusion reads that comprise an intragenic fusion breakpoint; and detecting an alignment error by identifying a subset of one or more of the gene fusion reads that comprise genetic variants within a region comprising the intragenic fusion breakpoint, wherein the region comprises one or more nucleotides adjacent to the intragenic fusion breakpoint.

In certain aspects, the present disclosure provides a method for suppressing alignment errors in detecting a true genetic variant in cell-free DNA molecules from a sample of a subject, comprising: sequencing cell-free DNA molecules from the sample of the subject, wherein each of the cell-free DNA molecules generates a plurality of sequence reads; aligning sequence reads derived from the sequencing to a reference sequence to produce aligned sequence reads; identifying, from the aligned sequence reads, a set of gene fusion reads that comprise an intragenic fusion breakpoint; detecting an alignment error by identifying a subset of one or more of the gene fusion reads that comprise genetic variants within a region comprising the intragenic fusion breakpoint, wherein the region comprises one or more nucleotides adjacent to the intragenic fusion breakpoint; filtering out at least a portion of the one or more detected alignment errors in the subset of the one or more gene fusion reads to produce filtered sequence reads; and detecting filtered sequence reads that include a true genetic variant as compared to the reference sequence.

In certain aspects, the present disclosure provides a method for suppressing alignment errors in detecting a true genetic variant in cell-free DNA molecules from a sample of a subject, comprising: sequencing cell-free DNA molecules from the sample of the subject, wherein each of the cell-free DNA molecules generates a plurality of sequence reads; aligning sequence reads derived from the sequencing to a reference sequence to produce aligned sequence reads; identifying, from the aligned sequence reads, a set of gene fusion reads that comprise an intragenic fusion breakpoint; detecting an alignment error by identifying a subset of one or more of the gene fusion reads that comprise genetic variants, wherein the subset of the one or more of the gene fusion reads comprises a genetic sequence corresponding to SMAD4 and/or RAF1; filtering out at least a portion of the one or more detected alignment errors in the subset of the one or more of the gene fusion reads to produce filtered sequence reads; and detecting filtered sequence reads that include a true genetic variant as compared to the reference sequence.

In certain aspects, the present disclosure provides a method for detecting alignment errors in genetic sequence reads, comprising: sequencing cell-free DNA molecules from a sample of a subject, wherein each of the cell-free DNA molecules generates a plurality of sequence reads; aligning sequence reads derived from the sequencing to a reference sequence to produce aligned sequence reads; determining, from the aligned sequence reads, a set of gene fusion reads that comprise an intragenic fusion breakpoint; determining a subset of one or more of the gene fusion reads that comprise genetic variants within a region comprising the intragenic fusion breakpoint, wherein the region comprises one or more nucleotides adjacent to the intragenic fusion breakpoint; and identifying each genetic variant within the region meeting a predetermined criterion as an alignment error.

In certain aspects, the present disclosure provides a method for suppressing alignment errors in detecting a true genetic variant in cell-free DNA molecules from a sample of a subject, comprising: sequencing cell-free DNA molecules from the sample of the subject, wherein each of the cell-free DNA molecules generates a plurality of sequence reads; aligning sequence reads derived from the sequencing to a reference sequence to produce aligned sequence reads; determining, from the aligned sequence reads, a set of gene fusion reads that comprise an intragenic fusion breakpoint; determining a subset of one or more of the gene fusion reads that comprise genetic variants within a region comprising the intragenic fusion breakpoint, wherein the region comprises one or more nucleotides adjacent to the intragenic fusion breakpoint; identifying each genetic variant within the region meeting a predetermined criterion as an alignment error; filtering out one or more alignment errors in the subset of the one or more gene fusion reads to produce filtered sequence reads; and detecting filtered sequence reads that include a true genetic variant as compared to the reference sequence.

In certain aspects, the present disclosure provides a method for detecting alignment errors in genetic sequence reads at least partially using a computer, comprising: receiving, by the computer, sequence information comprising the genetic sequence reads obtained from cell-free nucleic acid molecules in a biological sample from a subject; aligning the genetic sequence reads to a reference sequence to produce aligned sequence reads; identifying, from the aligned sequence reads, a set of gene fusion reads that comprise an intragenic fusion breakpoint; and detecting an alignment error by identifying a subset of one or more of the gene fusion reads that comprise genetic variants within a region comprising the intragenic fusion breakpoint, wherein the region comprises one or more nucleotides adjacent to the intragenic fusion breakpoint.

In certain aspects, the present disclosure provides a method for suppressing alignment errors in detecting a true genetic variant in cell-free nucleic acid molecules from a biological sample of a subject at least partially using a computer, comprising: receiving, by the computer, sequence information comprising sequence reads obtained from the cell-free nucleic acid molecules; aligning the sequence reads to a reference sequence to produce aligned sequence reads; identifying, from the aligned sequence reads, a set of gene fusion reads that comprise an intragenic fusion breakpoint; detecting an alignment error by identifying a subset of one or more of the gene fusion reads that comprise genetic variants within a region comprising the intragenic fusion breakpoint, wherein the region comprises one or more nucleotides adjacent to the intragenic fusion breakpoint; filtering out at least a portion of the one or more detected alignment errors in the subset of the one or more gene fusion reads to produce filtered sequence reads; and detecting filtered sequence reads that include a true genetic variant as compared to the reference sequence.

In certain aspects, the present disclosure provides a method for suppressing alignment errors in detecting a true genetic variant in cell-free nucleic acid molecules from a sample of a subject at least partially using a computer, comprising: receiving, by the computer, sequence information comprising sequencing reads obtained from the cell-free nucleic acid molecules; aligning the sequence reads to a reference sequence to produce aligned sequence reads; identifying, from the aligned sequence reads, a set of gene fusion reads that comprise an intragenic fusion breakpoint; detecting an alignment error by identifying a subset of one or more of the gene fusion reads that comprise genetic variants, wherein the subset of the one or more of the gene fusion reads comprises a genetic sequence corresponding to SMAD4, TYRO3, and/or RAF1; filtering out at least a portion of the one or more detected alignment errors in the subset of the one or more of the gene fusion reads to produce filtered sequence reads; and detecting filtered sequence reads that include a true genetic variant as compared to the reference sequence.

In certain aspects, the present disclosure provides a method for detecting alignment errors in genetic sequence reads at least partially using a computer, comprising: receiving, by the computer, sequence information comprising the genetic sequence reads obtained from cell-free nucleic acid molecules in a biological sample from a subject; aligning the genetic sequence reads to a reference sequence to produce aligned sequence reads; determining, from the aligned sequence reads, a set of gene fusion reads that comprise an intragenic fusion breakpoint; determining a subset of one or more of the gene fusion reads that comprise genetic variants within a region comprising the intragenic fusion breakpoint, wherein the region comprises one or more nucleotides adjacent to the intragenic fusion breakpoint; and identifying each genetic variant within the region meeting a predetermined criterion as an alignment error.

In certain aspects, the present disclosure provides a method for suppressing alignment errors in detecting a true genetic variant in cell-free nucleic acid molecules from a sample of a subject at least partially using a computer, comprising: receiving, by the computer, sequence information comprising sequencing reads obtained from the cell-free nucleic acid molecules; aligning the sequence reads to a reference sequence to produce aligned sequence reads; identifying, from the aligned sequence reads, a set of gene fusion reads that comprise an intragenic fusion breakpoint; detecting an alignment error by identifying a subset of one or more of the gene fusion reads that comprise genetic variants, wherein the subset of the one or more of the gene fusion reads comprises a genetic sequence corresponding to SMAD4, TYRO3, and/or RAF1; filtering out at least a portion of the one or more detected alignment errors in the subset of the one or more of the gene fusion reads to produce filtered sequence reads; and detecting filtered sequence reads that include a true genetic variant as compared to the reference sequence.

In certain embodiments, the set of the gene fusion reads corresponds to one or more processed pseudogenes (PPGs). In certain embodiments, the one or more PPGs comprise one or more sample-specific PPGs. In certain embodiments, the one or more PPGs are not present in the reference genome either due to gaps in the reference genome or because they are sample-specific PPGs. In certain embodiments, the one or more sample-specific PPGs identify the subject in a population of subjects. In certain embodiments, the one or more PPGs are derived from exonic sequences of genes from the group consisting of: SMAD4, GNAS, TP53, RAF1, CDK4, TYRO3, MAPK1, STK11, CCND1, HRAS, MET, MYC, and NRAS. In certain embodiments, the one or more PPGs comprise two or more PPGs derived from one or more sequences from the group consisting of: SMAD4, GNAS, TP53, RAF1, CDK4, TYRO3, MAPK1, STK11, CCND1, HRAS, MET, MYC, and NRAS. In certain embodiments, the one or more PPGs comprise three or more PPGs derived from one or more sequences from the group consisting of: SMAD4, GNAS, TP53, RAF1, CDK4, TYRO3, MAPK1, STK11, CCND1, HRAS, MET, MYC, and NRAS.

In certain embodiments, the genetic variants or true genetic variant comprise a single nucleotide variant (SNV) or an insertion or deletion (indel). In certain embodiments, the genetic variants comprise an SNV. In certain embodiments, the SNV is located at an intron-exon boundary. In certain embodiments, the SNV is located within a gene coding sequence (CDS). In certain embodiments, the genetic variants comprise an indel.

In certain embodiments, the region comprises about 2, 4, 6, 8, 10, 15, or 20 nucleotides adjacent to the intragenic fusion breakpoint. In certain embodiments, the region is fewer than about 100, 50, 20, 15, 10, 8, 6, 4, 2 nucleotides from the fusion breakpoint. In certain embodiments, the portion of the one or more detected alignment errors is filtered out based on the detected alignment errors having a mutant allele fraction in the sample which is less than or equal to a mutant allele fraction of the intragenic fusion corresponding to the intragenic fusion breakpoint in the sample. In certain embodiments, the portion of the one or more detected alignment errors is filtered out based on the gene fusion reads that comprise genetic variants not belonging to a pre-defined set of clinically actionable variants.

In certain embodiments, the sample is a bodily fluid sample selected from the group consisting of blood, plasma, serum, urine, saliva, mucosal excretions, sputum, stool, and tears. In certain embodiments, the subject has a disease or disorder. In certain embodiments, the disease is cancer.

In certain embodiments, the method comprises isolating cell-free nucleic acid molecules from the biological sample of the subject. In certain embodiments, the cell-free nucleic acid molecules comprise DNA, RNA, or a combination of these. In certain embodiments, the cell-free nucleic acid molecules are cell-free DNA. In certain embodiments, the cell-free nucleic acid molecules are double-stranded DNA.

In certain embodiments, the method comprises attaching one or more adapters comprising molecular barcodes to the cell-free nucleic acid molecules prior to sequencing to generate tagged parent polynucleotides. In certain embodiments, the adapters are attached to both ends of the cell-free nucleic acid molecules. In certain embodiments, the cell-free nucleic acid molecules are uniquely barcoded. In certain embodiments, the cell-free nucleic acid molecules are non-uniquely barcoded. In certain embodiments, each barcode comprises a fixed or semi-random oligonucleotide sequence that in combination with a diversity of molecules sequenced from a selected region enables identification of unique molecules.

In certain embodiments, the method comprises amplifying the tagged parent polynucleotides to generate progeny polynucleotides. In certain embodiments, the method comprises selectively enriching the progeny polynucleotides for a target sequence of interest, thereby generating enriched progeny polynucleotides. In certain embodiments, the method comprises amplifying the enriched progeny polynucleotides. In certain embodiments, the method comprises tagging the progeny polynucleotides or enriched progeny polynucleotides with a sample index sequence.

In certain embodiments, the sequence information is obtained from a nucleic acid sequencer. In certain embodiments, the set of gene fusion reads is identified by aligning and connecting sequenced paired-end reads. In certain embodiments, the set of gene fusion reads is identified based on a discontinuity in coverage across an intron-exon boundary. In certain embodiments, the pre-defined set comprises variants found in COSMIC, The Cancer Genome Atlas (TCGA), or the Exome Aggregation Consortium (ExAC).

In certain embodiments, the present methods can be computer-implemented, such that any or all of the steps described in the specification or appended claims other than wet chemistry steps can be performed in a suitable programmed computer.

In certain aspects, the present disclosure provides a system, comprising a controller comprising, or capable of accessing, computer readable media comprising non-transitory computer-executable instructions which, when executed by at least one electronic processor, perform a method for detecting alignment errors in genetic sequence reads, the method comprising: receiving sequence information comprising the genetic sequence reads obtained from cell-free nucleic acid molecules in a biological sample from a subject; aligning the genetic sequence reads to a reference sequence to produce aligned sequence reads; identifying, from the aligned sequence reads, a set of gene fusion reads that comprise an intragenic fusion breakpoint; and detecting an alignment error by identifying a subset of one or more of the gene fusion reads that comprise genetic variants within a region comprising the intragenic fusion breakpoint, wherein the region comprises one or more nucleotides adjacent to the intragenic fusion breakpoint.

In certain aspects, the present disclosure provides a system, comprising a controller comprising, or capable of accessing, computer readable media comprising non-transitory computer-executable instructions which, when executed by at least one electronic processor, perform a method for suppressing alignment errors in detecting a true genetic variant in cell-free nucleic acid molecules from a biological sample of a subject, the method comprising: receiving sequence information comprising sequence reads obtained from the cell-free nucleic acid molecules; aligning the sequence reads to a reference sequence to produce aligned sequence reads; identifying, from the aligned sequence reads, a set of gene fusion reads that comprise an intragenic fusion breakpoint; detecting an alignment error by identifying a subset of one or more of the gene fusion reads that comprise genetic variants within a region comprising the intragenic fusion breakpoint, wherein the region comprises one or more nucleotides adjacent to the intragenic fusion breakpoint; filtering out at least a portion of the one or more detected alignment errors in the subset of the one or more gene fusion reads to produce filtered sequence reads; and detecting filtered sequence reads that include a true genetic variant as compared to the reference sequence.

In certain aspects, the present disclosure provides a system, comprising a controller comprising, or capable of accessing, computer readable media comprising non-transitory computer-executable instructions which, when executed by at least one electronic processor, perform a method for suppressing alignment errors in detecting a true genetic variant in cell-free nucleic acid molecules from a sample of a subject, the method comprising: receiving sequence information comprising sequencing reads obtained from the cell-free nucleic acid molecules; aligning the sequence reads to a reference sequence to produce aligned sequence reads; identifying, from the aligned sequence reads, a set of gene fusion reads that comprise an intragenic fusion breakpoint; detecting an alignment error by identifying a subset of one or more of the gene fusion reads that comprise genetic variants, wherein the subset of the one or more of the gene fusion reads comprises a genetic sequence corresponding to SMAD4, TYRO3, and/or RAF1; filtering out at least a portion of the one or more detected alignment errors in the subset of the one or more of the gene fusion reads to produce filtered sequence reads; and detecting filtered sequence reads that include a true genetic variant as compared to the reference sequence.

In certain aspects, the present disclosure provides a system, comprising a controller comprising, or capable of accessing, computer readable media comprising non-transitory computer-executable instructions which, when executed by at least one electronic processor, perform a method for detecting alignment errors in genetic sequence reads, the method comprising: receiving sequence information comprising the genetic sequence reads obtained from cell-free nucleic acid molecules in a biological sample from a subject; aligning the genetic sequence reads to a reference sequence to produce aligned sequence reads; determining, from the aligned sequence reads, a set of gene fusion reads that comprise an intragenic fusion breakpoint; determining a subset of one or more of the gene fusion reads that comprise genetic variants within a region comprising the intragenic fusion breakpoint, wherein the region comprises one or more nucleotides adjacent to the intragenic fusion breakpoint; and identifying each genetic variant within the region meeting a predetermined criterion as an alignment error.

In certain aspects, the present disclosure provides a system, comprising a controller comprising, or capable of accessing, computer readable media comprising non-transitory computer-executable instructions which, when executed by at least one electronic processor, perform a method for suppressing alignment errors in detecting a true genetic variant in cell-free nucleic acid molecules from a sample of a subject, the method comprising: receiving sequence information comprising sequence reads obtained from cell-free nucleic acid molecules in a biological sample from a subject; aligning the sequence reads to a reference sequence to produce aligned sequence reads; determining, from the aligned sequence reads, a set of gene fusion reads that comprise an intragenic fusion breakpoint; determining a subset of one or more of the gene fusion reads that comprise genetic variants within a region comprising the intragenic fusion breakpoint, wherein the region comprises one or more nucleotides adjacent to the intragenic fusion breakpoint; identifying each genetic variant within the region meeting a predetermined criterion as an alignment error; filtering out one or more alignment errors in the subset of the one or more gene fusion reads to produce filtered sequence reads; and detecting filtered sequence reads that include a true genetic variant as compared to the reference sequence.

In certain aspects, the present disclosure provides a method of producing a filtered sequence information data set at least partially using a computer, the method comprising: (a) receiving test sequence information comprising test sequence reads obtained from cfDNA in a biological sample obtained from a subject; (b) identifying one or more split sequence reads among the test sequence reads, wherein each split sequence read comprises at least one breakpoint; and, (c) suppressing, in the test sequence information, at least a portion of one or more of the split sequence reads and/or at least a portion of one or more of the test sequence reads that comprise at least one sequence variant within a selected number of nucleotides from a given breakpoint, thereby producing the filtered sequence information data set.

In certain aspects, the present disclosure provides a method of producing a filtered sequence information data set at least partially using a computer, the method comprising: (a) identifying one or more split sequence reads in a set of test sequence reads obtained from cfDNA in a biological sample obtained from a subject, wherein each split sequence read comprises at least one breakpoint; and, (b) suppressing, in the set of test sequence reads, at least a portion of one or more of the split sequence reads and/or at least a portion of one or more of the test sequence reads that comprise at least one sequence variant within a selected number of nucleotides from a given breakpoint, thereby producing the filtered sequence information data set.

In certain aspects, the present disclosure provides a method of producing a filtered sequence information data set at least partially using a computer, the method comprising: (a) identifying one or more split sequence reads in a set of test sequence reads obtained from cfDNA in a biological sample obtained from a subject, wherein each split sequence read comprises at least one breakpoint; and, (b) suppressing, in the set of test sequence reads, one or more base calls of the split sequence reads and/or one or more base calls of the test sequence reads that comprise at least one sequence variant within a selected number of nucleotides from a given breakpoint, thereby producing the filtered sequence information data set.

In certain aspects, the present disclosure provides a method of producing a filtered sequence information data set at least partially using a computer, the method comprising: (a) receiving test sequence information comprising test sequence reads obtained from cfDNA in a biological sample obtained from a subject; (b) identifying one or more split sequence reads among the test sequence reads, wherein each split sequence read comprises at least one breakpoint; and, (c) suppressing, in the test sequence information, one or more base calls of the split sequence reads and/or one or more base calls of the test sequence reads that comprise at least one sequence variant within a selected number of nucleotides from a given breakpoint, thereby producing the filtered sequence information data set.

In certain aspects, the present disclosure provides a method of producing a filtered sequence information data set at least partially using a computer, the method comprising: (a) identifying one or more split sequence reads in a set of test sequence reads obtained from cell-free nucleic acid (cfNA) in a biological sample obtained from a subject, wherein each split sequence read comprises at least one breakpoint; and, (b) suppressing, in the set of test sequence reads, at least a portion of one or more of the split sequence reads and/or at least a portion of one or more of the test sequence reads that comprise at least one sequence variant within a selected number of nucleotides from a given breakpoint, thereby producing the filtered sequence information data set.

In certain aspects, the present disclosure provides a method of producing a filtered sequence information data set at least partially using a computer, the method comprising: (a) identifying one or more split sequence reads in a set of test sequence reads obtained from cell-free nucleic acid (cfNA) in a biological sample obtained from a subject, wherein each split sequence read comprises at least one breakpoint; and, (b) suppressing, in the set of test sequence reads, one or more base calls of the split sequence reads and/or one or more base calls of the test sequence reads that comprise at least one sequence variant within a selected number of nucleotides from a given breakpoint, thereby producing the filtered sequence information data set.

In certain aspects, the present disclosure provides a method of producing a filtered sequence information data set, the method comprising: (a) sequencing cell-free deoxyribonucleic acid (cfDNA) in a biological sample obtained from a subject to produce a set of test sequence reads; (b) identifying one or more split sequence reads in the set of test sequence reads, wherein each split sequence read comprises at least one breakpoint; and, (c) suppressing, in the set of test sequence reads, at least a portion of one or more of the split sequence reads and/or at least a portion of one or more of the test sequence reads that comprise at least one sequence variant within a selected number of nucleotides from a given breakpoint, thereby producing the filtered sequence information data set.

In certain aspects, the present disclosure provides a method of detecting a target sequence variant at least partially using a computer, the method comprising: (a) identifying one or more split sequence reads in a set of test sequence reads obtained from cfDNA in a biological sample obtained from a subject, wherein each split sequence read comprises at least one breakpoint; (b) suppressing, in the set of test sequence reads, at least a portion of one or more of the split sequence reads and/or at least a portion of one or more of the test sequence reads that comprise at least one non-target sequence variant within a selected number of nucleotides from a given breakpoint to produce a filtered sequence information data set; and, (c) identifying at least one target test sequence read in the filtered sequence information data set that comprises the target sequence variant, thereby detecting the target sequence variant.

In certain aspects, the present disclosure provides a method of treating a disease, disorder, or condition in a subject, the method comprising: (a) identifying one or more split sequence reads in a set of test sequence reads obtained from cfDNA in a biological sample obtained from the subject, wherein each split sequence read comprises at least one breakpoint; (b) suppressing, in the set of test sequence reads, at least a portion of one or more of the split sequence reads and/or at least a portion of one or more of the test sequence reads that comprise at least one non-target sequence variant within a selected number of nucleotides from a given breakpoint to produce a filtered sequence information data set; (c) identifying at least one target test sequence read in the filtered sequence information data set that comprises a target sequence variant indicative of the disease, disorder, or condition in the subject; and, (d) administering one or more therapies to the subject that are effective in treating the disease, disorder, or condition, thereby treating the disease, disorder, or condition in the subject.

In certain embodiments, the method comprises suppressing one or more additional test sequence reads that comprise one or more sequence variants that are not within the selected number of nucleotides from the given breakpoint when the additional test sequence reads align with at least a portion of one or more gene sequences selected from the group consisting of: SMAD4, GNAS, TP53, RAF1, CDK4, TYRO3, MAPK1, STK11, CCND1, HRAS, MET, MYC, and NRAS.

In certain embodiments, identifying a given split sequence read in comprises identifying test sequence reads that only partially align with reference sequence information. In certain embodiments, identifying a given split sequence read comprises identifying an increased coverage of one or more genomic regions in the test sequence information relative to reference sequence information that lacks split sequence reads comprising the one or more genomic regions.

In certain embodiments, the one or more genomic regions comprise at least one coding sequence (CDS). In certain embodiments, identifying a given split sequence read comprises identifying at least two split sequence reads that differ from one another and each comprise an identical breakpoint. In certain embodiments, the method comprises identifying at least one target test sequence read in the filtered sequence information data set. In certain embodiments, the target test sequence read comprises a target sequence variant indicative of a given disease, disorder, or condition in the subject. In certain embodiments, the method comprises treating the given disease, disorder, or condition in the subject.

In certain embodiments, the one or more of the suppressed split sequence reads comprise at least a portion of a processed pseudogene (PPG). In certain embodiments, the method comprises removing, from the test sequence information, the split sequence reads and/or the test sequence reads that comprise the sequence variant within the selected number of nucleotides from the given breakpoint.

In certain aspects, the present disclosure provides a system, comprising a controller comprising, or capable of accessing, computer readable media comprising non-transitory computer-executable instructions which, when executed by at least one electronic processor perform at least: (a) receiving test sequence information comprising test sequence reads obtained from cfDNA in a biological sample obtained from a subject; (b) identifying one or more split sequence reads among the test sequence reads, wherein each split sequence read comprises at least one breakpoint; and, (c) suppressing, in the test sequence information, at least a portion of one or more of the split sequence reads and/or at least a portion of one or more of the test sequence reads that comprise at least one sequence variant within a selected number of nucleotides from a given breakpoint.

In certain aspects, the present disclosure provides a system, comprising a controller comprising, or capable of accessing, computer readable media comprising non-transitory computer-executable instructions which, when executed by at least one electronic processor perform at least: (a) identifying one or more split sequence reads in a set of test sequence reads obtained from cfDNA in a biological sample obtained from a subject, wherein each split sequence read comprises at least one breakpoint; and, (b) suppressing, in the set of test sequence reads, at least a portion of one or more of the split sequence reads and/or at least a portion of one or more of the test sequence reads that comprise at least one sequence variant within a selected number of nucleotides from a given breakpoint.

In certain aspects, the present disclosure provides a system, comprising a controller comprising, or capable of accessing, computer readable media comprising non-transitory computer-executable instructions which, when executed by at least one electronic processor perform at least: (a) identifying one or more split sequence reads in a set of test sequence reads obtained from cfDNA in a biological sample obtained from a subject, wherein each split sequence read comprises at least one breakpoint; and, (b) suppressing, in the set of test sequence reads, one or more base calls of the split sequence reads and/or one or more base calls of the test sequence reads that comprise at least one sequence variant within a selected number of nucleotides from a given breakpoint.

In certain aspects, the present disclosure provides a system, comprising a controller comprising, or capable of accessing, computer readable media comprising non-transitory computer-executable instructions which, when executed by at least one electronic processor perform at least: (a) receiving test sequence information comprising test sequence reads obtained from cfDNA in a biological sample obtained from a subject; (b) identifying one or more split sequence reads among the test sequence reads, wherein each split sequence read comprises at least one breakpoint; and, (c) suppressing, in the test sequence information, one or more base calls of the split sequence reads and/or one or more base calls of the test sequence reads that comprise at least one sequence variant within a selected number of nucleotides from a given breakpoint.

In certain aspects, the present disclosure provides a system, comprising a controller comprising, or capable of accessing, computer readable media comprising non-transitory computer-executable instructions which, when executed by at least one electronic processor perform at least: (a) identifying one or more split sequence reads in a set of test sequence reads obtained from cell-free nucleic acid (cfNA) in a biological sample obtained from a subject, wherein each split sequence read comprises at least one breakpoint; and, (b) suppressing, in the set of test sequence reads, at least a portion of one or more of the split sequence reads and/or at least a portion of one or more of the test sequence reads that comprise at least one sequence variant within a selected number of nucleotides from a given breakpoint.

In certain aspects, the present disclosure provides a system, comprising a controller comprising, or capable of accessing, computer readable media comprising non-transitory computer-executable instructions which, when executed by at least one electronic processor perform at least: (a) identifying one or more split sequence reads in a set of test sequence reads obtained from cfNA in a biological sample obtained from a subject, wherein each split sequence read comprises at least one breakpoint; and, (b) suppressing, in the set of test sequence reads, one or more base calls of the split sequence reads and/or one or more base calls of the test sequence reads that comprise at least one sequence variant within a selected number of nucleotides from a given breakpoint.

In certain aspects, the present disclosure provides a system, comprising a controller comprising, or capable of accessing, computer readable media comprising non-transitory computer-executable instructions which, when executed by at least one electronic processor perform at least: (a) sequencing cfDNA in a biological sample obtained from a subject to produce a set of test sequence reads; (b) identifying one or more split sequence reads in the set of test sequence reads, wherein each split sequence read comprises at least one breakpoint; and, (c) suppressing, in the set of test sequence reads, at least a portion of one or more of the split sequence reads and/or at least a portion of one or more of the test sequence reads that comprise at least one sequence variant within a selected number of nucleotides from a given breakpoint.

In certain aspects, the present disclosure provides a system, comprising a controller comprising, or capable of accessing, computer readable media comprising non-transitory computer-executable instructions which, when executed by at least one electronic processor perform at least: (a) identifying one or more split sequence reads in a set of test sequence reads obtained from cfDNA in a biological sample obtained from a subject, wherein each split sequence read comprises at least one breakpoint; (b) suppressing, in the set of test sequence reads, at least a portion of one or more of the split sequence reads and/or at least a portion of one or more of the test sequence reads that comprise at least one non-target sequence variant within a selected number of nucleotides from a given breakpoint to produce a filtered sequence information data set; and, (c) identifying at least one target test sequence read in the filtered sequence information data set that comprises the target sequence variant.

In certain aspects, the present disclosure provides a computer readable media comprising non-transitory computer-executable instructions which, when executed by at least one electronic processor perform at least: (a) receiving test sequence information comprising test sequence reads obtained from cell-free deoxyribonucleic acid (cfDNA) in a biological sample obtained from a subject; (b) identifying one or more split sequence reads among the test sequence reads, wherein each split sequence read comprises at least one breakpoint; and, (c) suppressing, in the test sequence information, at least a portion of one or more of the split sequence reads and/or at least a portion of one or more of the test sequence reads that comprise at least one sequence variant within a selected number of nucleotides from a given breakpoint.

In certain aspects, the present disclosure provides a computer readable media comprising non-transitory computer-executable instructions which, when executed by at least one electronic processor perform at least: (a) identifying one or more split sequence reads in a set of test sequence reads obtained from cfDNA in a biological sample obtained from a subject, wherein each split sequence read comprises at least one breakpoint; and, (b) suppressing, in the set of test sequence reads, at least a portion of one or more of the split sequence reads and/or at least a portion of one or more of the test sequence reads that comprise at least one sequence variant within a selected number of nucleotides from a given breakpoint.

In certain aspects, the present disclosure provides a computer readable media comprising non-transitory computer-executable instructions which, when executed by at least one electronic processor perform at least: (a) identifying one or more split sequence reads in a set of test sequence reads obtained from cfDNA in a biological sample obtained from a subject, wherein each split sequence read comprises at least one breakpoint; and, (b) suppressing, in the set of test sequence reads, one or more base calls of the split sequence reads and/or one or more base calls of the test sequence reads that comprise at least one sequence variant within a selected number of nucleotides from a given breakpoint.

In certain aspects, the present disclosure provides a computer readable media comprising non-transitory computer-executable instructions which, when executed by at least one electronic processor perform at least: (a) receiving test sequence information comprising test sequence reads obtained from cfDNA in a biological sample obtained from a subject; (b) identifying one or more split sequence reads among the test sequence reads, wherein each split sequence read comprises at least one breakpoint; and, (c) suppressing, in the test sequence information, one or more base calls of the split sequence reads and/or one or more base calls of the test sequence reads that comprise at least one sequence variant within a selected number of nucleotides from a given breakpoint.

In certain aspects, the present disclosure provides a computer readable media comprising non-transitory computer-executable instructions which, when executed by at least one electronic processor perform at least: (a) identifying one or more split sequence reads in a set of test sequence reads obtained from cfNA in a biological sample obtained from a subject, wherein each split sequence read comprises at least one breakpoint; and, (b) suppressing, in the set of test sequence reads, at least a portion of one or more of the split sequence reads and/or at least a portion of one or more of the test sequence reads that comprise at least one sequence variant within a selected number of nucleotides from a given breakpoint.

In certain aspects, the present disclosure provides a computer readable media comprising non-transitory computer-executable instructions which, when executed by at least one electronic processor perform at least: (a) identifying one or more split sequence reads in a set of test sequence reads obtained from cfNA in a biological sample obtained from a subject, wherein each split sequence read comprises at least one breakpoint; and, (b) suppressing, in the set of test sequence reads, one or more base calls of the split sequence reads and/or one or more base calls of the test sequence reads that comprise at least one sequence variant within a selected number of nucleotides from a given breakpoint.

In certain aspects, the present disclosure provides a computer readable media comprising non-transitory computer-executable instructions which, when executed by at least one electronic processor perform at least: (a) sequencing cell-free deoxyribonucleic acid (cfDNA) in a biological sample obtained from a subject to produce a set of test sequence reads; (b) identifying one or more split sequence reads in the set of test sequence reads, wherein each split sequence read comprises at least one breakpoint; and, (c) suppressing, in the set of test sequence reads, at least a portion of one or more of the split sequence reads and/or at least a portion of one or more of the test sequence reads that comprise at least one sequence variant within a selected number of nucleotides from a given breakpoint.

In certain aspects, the present disclosure provides a computer readable media comprising non-transitory computer-executable instructions which, when executed by at least one electronic processor perform at least: (a) identifying one or more split sequence reads in a set of test sequence reads obtained from cfDNA in a biological sample obtained from a subject, wherein each split sequence read comprises at least one breakpoint; (b) suppressing, in the set of test sequence reads, at least a portion of one or more of the split sequence reads and/or at least a portion of one or more of the test sequence reads that comprise at least one non-target sequence variant within a selected number of nucleotides from a given breakpoint to produce a filtered sequence information data set; and, (c) identifying at least one target test sequence read in the filtered sequence information data set that comprises the target sequence variant.

DEFINITIONS

Figure 1:
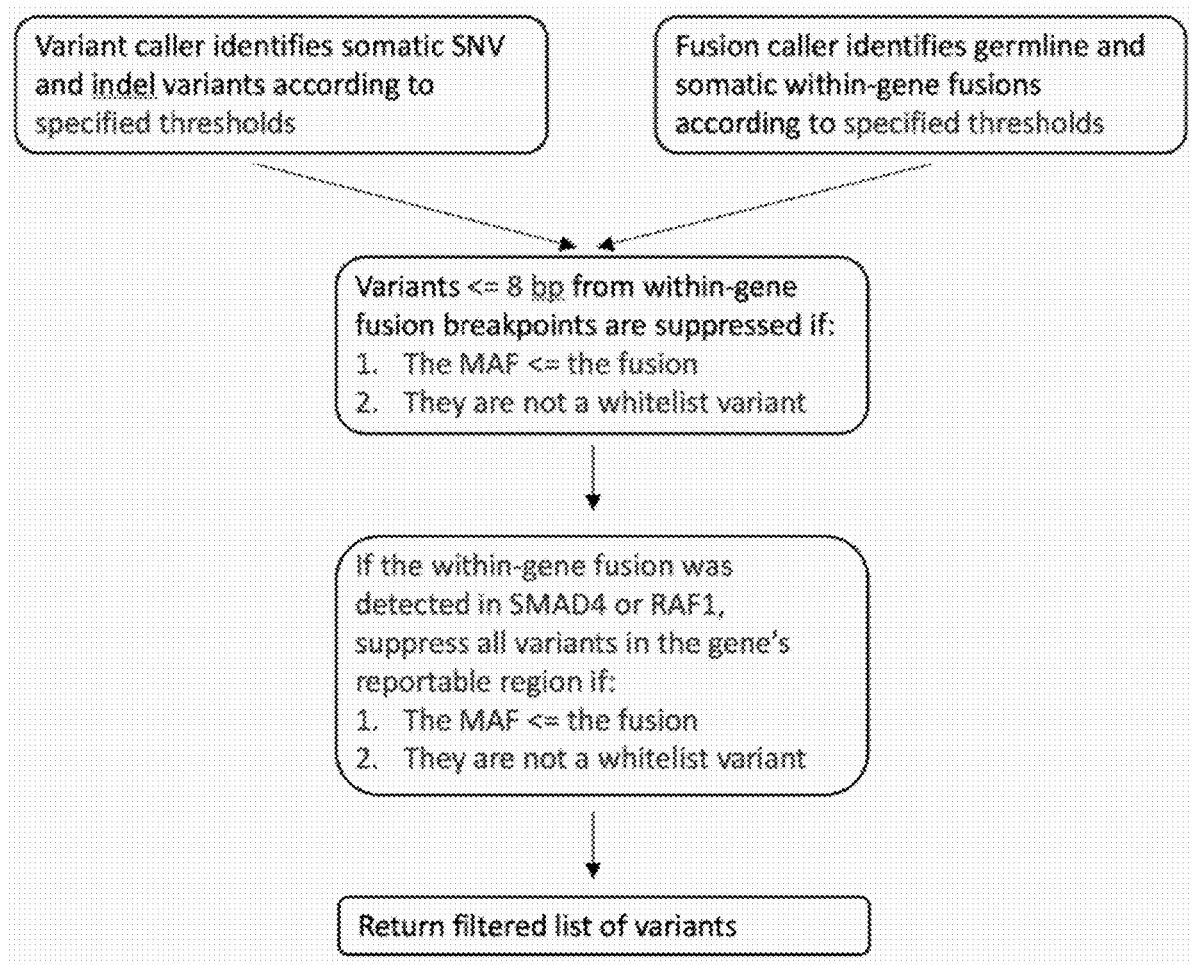
FIG. 1 is a diagram showing an exemplary method for detecting and suppressing an alignment error due to the presence of a processed pseudogene.

The term "subject" may refer to an animal, such as a mammalian species (preferably human) or avian (e.g., bird) species. More specifically, a subject can be a vertebrate, e.g., a mammal such as a mouse, a primate, a simian or a human. Animals include farm animals, sport animals, and pets. A subject can be a healthy individual, an individual that has symptoms or signs or is suspected of having a disease or a predisposition to the disease, or an individual that is in need of therapy or suspected of needing therapy. In some embodiments, the subject is human, such as a human who has, or is suspected of having, cancer.

The phrase "cell-free nucleic acid" may refer to nucleic acids not contained within or otherwise bound to a cell, or in other words, nucleic acids remaining in a sample after removing intact cells. Cell-free nucleic acids can be referred to as non-encapsulated nucleic acid sourced from a bodily fluid (e.g., blood, urine, CSF, etc.) from a subject. Cell-free nucleic acids include DNA (cfDNA), RNA (cfRNA), and hybrids thereof, including genomic DNA, mitochondrial DNA, circulating DNA, siRNA, miRNA, circulating RNA (cRNA), tRNA, rRNA, small nucleolar RNA (snoRNA), Piwi-interacting RNA (piRNA), long non-coding RNA (long ncRNA), or fragments of any of these. Cell-free nucleic acids can be double-stranded, single-stranded, or partially double- and single-stranded. A cell-free nucleic acid can be released into bodily fluid through secretion or cell death processes, e.g., cellular necrosis and apoptosis. Some cell-free nucleic acids are released into bodily fluid from cancer cells e.g., circulating tumor DNA (ctDNA). Others are released from healthy cells. ctDNA can be non-encapsulated tumor-derived fragmented DNA. Cell-free fetal DNA (cffDNA) is fetal DNA circulating freely in the maternal blood stream. A cell-free nucleic acid can have one or more associated epigenetic modifications, for example, can be acetylated, 5-methylated, ubiquitylated, phosphorylated, sumoylated, ribosylated, and/or citrullinated. In some embodiments, cell-free nucleic acid is cfDNA, which usually includes double-stranded cfDNA.

The phrase "nucleic acid tag" may refer to a short nucleic acid (e.g., less than 500, 100, 50, or 10 nucleotides long), used to label nucleic acid molecules to distinguish nucleic acids from different samples (e.g., representing a sample index), or different nucleic acid molecules in the same sample (e.g., representing a molecular barcode), of different types, or which have undergone different processing. Tags can be single stranded, double-stranded or at least partially double-stranded. Tags can have the same length or varied lengths. Tags can be blunt-end or have an overhang. Tags can be attached to one end or both ends of the nucleic acids. Nucleic acid tags can be decoded to reveal information such as the sample of origin, form or processing of a nucleic acid. Tags can be used to allow pooling and parallel processing of multiple samples comprising nucleic acids bearing different molecule tags and/or sample indexes with the nucleic acids subsequently being deconvoluted by reading the molecule tags. Additionally or alternatively, nucleic acid tags can be used to distinguish different molecules in the same sample (i.e., molecular barcode). This includes both uniquely tagging different molecules in the sample, or non-uniquely tagging the molecules in the sample. In the case of non-unique tagging, a limited number of different tags may be used to tag molecules such that different molecules can be distinguished based on their start and/or stop position where they map on a reference genome (i.e., genomic coordinates) in combination with at least one tag. Typically then, a sufficient number of different tags are used such that there is a low probability (e.g. <10%, <5%, <1%, or <0.1%) that any two molecules having the same start/stop also have the same tag. Some tags include multiple identifiers to label samples, forms of molecule within a sample, and molecules within a form having the same start and stop points. Such tags can exist in the form Ali, wherein the letter indicates a sample type, the Arabic number indicates a form of molecule within a sample, and the Roman numeral indicates a molecule within a form.

The term "adapter" refers to a short nucleic acid (e.g., less than 500, 100, or 50 nucleotides long) usually at least partly double-stranded for linkage to either or both ends of a sample nucleic acid molecule. Adapters can include primer binding sites to permit amplification of a nucleic acid molecule flanked by adapters at both ends, and/or a sequencing primer binding site, including primer binding sites for next generation sequencing (NGS). Adapters can also include binding sites for capture probes, such as an oligonucleotide attached to a flow cell support. Adapters can also include a tag as described above. Tags are preferably positioned relative to primer and sequencing primer binding sites, such that a tag is included in amplicons and sequencing reads of a nucleic acid molecule. Adapters of the same or different sequences can be linked to the respective ends of a nucleic acid molecule. Sometimes adapters of the same sequence are linked to the respective ends except that the barcode is different. A preferred adapter is a Y-shaped adapter in which one end is blunt ended or tailed, for joining to a nucleic acid molecule, which is also blunt ended or tailed with one or more complementary nucleotides. Another preferred adapter is a bell-shaped adapter, likewise with a blunt or tailed end for joining to a nucleic acid to be analyzed.

As used herein, the terms "sequencing" or "sequencer" refer to any of a number of technologies used to determine the sequence of a biomolecule, e.g., a nucleic acid such as DNA or RNA. Exemplary sequencing methods include, but are not limited to, targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and a combination thereof. In some embodiments, sequencing can be performed by a gene analyzer such as, for example, gene analyzers commercially available from Illumina or Applied Biosystems.

The phrase "next generation sequencing" or NGS refers to sequencing technologies having increased throughput as compared to traditional Sanger- and capillary electrophoresis-based approaches, for example, with the ability to generate hundreds of thousands of relatively small sequence reads at a time. Some examples of next generation sequencing techniques include, but are not limited to, sequencing by synthesis, sequencing by ligation, and sequencing by hybridization.

The term "DNA (deoxyribonucleic acid)" refers to a chain of nucleotides comprising deoxyribonucleosides that each comprise one of four nucleobases, namely, adenine (A), thymine (T), cytosine (C), and guanine (G). The term "RNA (ribonucleic acid)" refers to a chain of nucleotides comprising four types of ribonucleosides that each comprise one of four nucleobases, namely; A, uracil (U), G, and C. Certain pairs of nucleotides specifically bind to one another in a complementary fashion (called complementary base pairing). In DNA, adenine (A) pairs with thymine (T) and cytosine (C) pairs with guanine (G). In RNA, adenine (A) pairs with uracil (U) and cytosine (C) pairs with guanine (G). When a first nucleic acid strand binds to a second nucleic acid strand made up of nucleotides that are complementary to those in the first strand, the two strands bind to form a double strand. As used herein, "nucleic acid sequencing data," "nucleic acid sequencing information," "nucleic acid sequence," "nucleotide sequence", "genomic sequence," "genetic sequence," or "fragment sequence," or "nucleic acid sequencing read" denotes any information or data that is indicative of the order of the nucleotide bases (e.g., adenine, guanine, cytosine, and thymine or uracil) in a molecule (e.g., a whole genome, whole transcriptome, exome, oligonucleotide, polynucleotide, or fragment) of a nucleic acid such as DNA or RNA. It should be understood that the present teachings contemplate sequence information obtained using all available varieties of techniques, platforms or technologies, including, but not limited to: capillary electrophoresis, microarrays, ligation-based systems, polymerase-based systems, hybridization-based systems, direct or indirect nucleotide identification systems, pyrosequencing, ion- or pH-based detection systems, and electronic signature-based systems.

A "polynucleotide", "nucleic acid", "nucleic acid molecule", or "oligonucleotide" refers to a linear polymer of nucleosides (including deoxyribonucleosides, ribonucleosides, or analogs thereof) joined by internucleosidic linkages. Typically, a polynucleotide comprises at least three nucleosides. Oligonucleotides often range in size from a few monomeric units, e.g. 3-4, to hundreds of monomeric units. Whenever a polynucleotide is represented by a sequence of letters, such as "ATGCCTG," it will be understood that the nucleotides are in 5'→3' order from left to right and that "A" denotes adenosine, "C" denotes cytosine, "G" denotes guanosine, and "T" denotes thymidine, unless otherwise noted. The letters A, C, G, and T may be used to refer to the bases themselves, to nucleosides, or to nucleotides comprising the bases, as is standard in the art.

The phrase "reference sequence" refers to a known sequence used for purposes of comparison with experimentally determined sequences. For example, a known sequence can be an entire genome, a chromosome, or any segment thereof. A reference typically includes at least 20, 50, 100, 200, 250, 300, 350, 400, 450, 500, 1000, or more nucleotides. A reference sequence can align with a single contiguous sequence of a genome or chromosome or can include non-contiguous segments aligning with different regions of a genome or chromosome. In some embodiments, the reference sequence is a human genome. Reference human genomes include, e.g., hG19 and hG38.

The term "pseudogene" generally refers to a segment of genomic DNA that is similar in its genetic sequence to a counterpart complete gene, but has lost at least some functionality in cellular gene expression or protein-coding ability. A pseudogene may have a high degree of homology or identity to its functional counterpart gene. In some embodiments, the pseudogene shares at least 40%, at least 45%, at least 50%, at least 55%, at least 60%, at least 65%, at least 70%, at least 75%, at least 80%, at least 85%, at least 90%, or at least 95% homology with a counterpart functional gene.

The phrase "processed pseudogene" generally refers to a pseudogene arising from the process of retrotransposition, whereby a complementary DNA (cDNA), a reverse transcribed mRNA transcript, is reintegrated into a new location in the genome. Processed pseudogenes commonly lack introns, thereby creating exon-exon intragenic (i.e., within-gene) fusions. Other characteristics of processed pseudogenes include poly-A tails, truncated 5' ends (compared to the counterpart complete gene), and lack of transcription machinery (e.g., promoter regions).

The phrase "biological sample" as used herein, generally refers to a tissue or fluid sample derived from a subject. A biological sample may be directly obtained from the subject. The biological sample may be or may include one or more nucleic acid molecules, such as deoxyribonucleic acid (DNA) or ribonucleic acid (RNA) molecules. The biological sample can be derived from any organ, tissue or biological fluid. A biological sample can comprise, for example, a bodily fluid or a solid tissue sample. An example of a solid tissue sample is a tumor sample, e.g., from a solid tumor biopsy. Bodily fluids include, for example, blood, serum, plasma, tumor cells, saliva, urine, lymphatic fluid, prostatic fluid, seminal fluid, milk, sputum, stool, tears, and derivatives of these. In some embodiments, the biological sample is, or is derived from, blood.

The phrase "mutant allele fraction", "mutation dose," or "MAF" refers to the fraction of nucleic acid molecules harboring an allelic alteration or mutation at a given genomic position in a given sample. MAF is generally expressed as a fraction or a percentage. For example, an MAF is typically less than about 0.5, 0.1, 0.05, or 0.01 (i.e., less than about 50%, 10%, 5%, or 1%) of all somatic variants or alleles present at a given locus.

The phrase "split sequence read" or "split read" or "gene fusion read" in the context of nucleic acid sequence information refers to a sequencing read that includes sub-sequences that map to different non-contiguous regions or loci of a given reference sequence. In certain embodiments, for example, a first sub-sequence of a given split sequence read maps to a first exon of a given gene of a reference sequence, while a second sub-sequence of that given split sequence read maps to a second exon of the same gene of the reference sequence, which first and second exons are separated by an intervening intron of the same gene of the reference sequence. In some of these embodiments, such a split sequence read is indicative of the presence of an intragenic fusion in the genome of a subject from whom the given split sequence read was obtained. In other exemplary embodiments, a first sub-sequence of a given split sequence read maps to an exon of a first gene of a reference sequence, while a second sub-sequence of that given split sequence read maps to an exon of a different second gene of the reference sequence, which exons are non-contiguous with one another in the reference sequence. In some of these embodiments, such a split sequence read is indicative of the presence of an intergenic fusion in the genome of a subject from whom the given split sequence read was obtained.

The term "breakpoint" in the context of a nucleic acid fusion molecule or a corresponding sequencing read refers to a terminal nucleotide position at a junction between fused sub-sequences of the nucleic acid fusion or represented in the corresponding sequencing read. For example, a given split sequence read may include a first sub-sequence that is contiguous with, and 5' to, a second sub-sequence in that split sequence read in which the first sub-sequence maps to a first locus in a reference sequence that is non-contiguous with a second locus in that reference sequence to which the second sub-sequence maps. In this example, the first sub-sequence of the split sequence read includes a breakpoint at its 3' terminal nucleotide, while the second sub-sequence of the split sequence read includes a breakpoint at its 5' terminal nucleotide. In certain applications, breakpoints such as these are referred to as a "breakpoint pair."

The phrase "administer" in the context of therapeutic agents (e.g., therapeutic nucleic acid constructs) means to give, apply or bring the agents into contact with a subject. Administration can be accomplished by any of a number of routes, including, for example, topical, oral, subcutaneous, intramuscular, intraperitoneal, intravenous, intrathecal and intradermal.

The phrase "about" or "approximately" as applied to one or more values or elements of interest, refers to a value or element that is similar to a stated reference value or element. In certain embodiments, the term "about" or "approximately" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

DETAILED DESCRIPTION

I. General Overview

A core challenge for clinical diagnostic sequencing tests is identifying genomic regions prone to short-read artefacts and mitigating their effects. Many of these regions have been identified through analysis of the human genome assembly; however, sample-specific fusion events, wherein the gross structure of wild-type chromosomes are altered to bring non-adjacent genomic regions into close proximity on the same chromosome, or artefacts of reverse-transcription, such as those produced by the presence of processed pseudogenes (PPGs), both germline and somatic, can produce false-positive variant calls at somatic allele frequencies if not properly identified. By identifying the signals produced by these fusion events on a sample-by-sample basis, the methods and systems disclosed herein can identify and eliminate an important source of clinically misleading variants while maintaining high specificity with minimal costs to sensitivity.

The methods and systems provided herein may be particularly useful in the analysis of nucleic acid molecules, in particular cell-free nucleic acid molecules. In some cases, cell-free nucleic acid molecules may be extracted and isolated from a biological sample from a subject. A biological sample may include a bodily fluid sample that is selected from the group including, but not limited to, blood, plasma, serum, urine, saliva, mucosal excretions, sputum, stool, and tears. Cell-free nucleic acid molecules can be extracted using a variety of methods known in the art, including but not limited to isopropanol precipitation and/or silica based purification.

The biological sample may be collected from a variety of subjects, such as subjects without a disease, subjects at risk for, showing symptoms of, or having a disease, such as cancer or a virus, or subjects at risk for, showing symptoms of, or having a genetic disorder. In some embodiments, the disease or disorder is selected from the group consisting of immune deficiency disorders, hemophilia, thalassemia, sickle cell disease, blood disease, chronic granulomatous disorder, congenital blindness, lysosomal storage disease, muscular dystrophy, cancer, neurodegenerative disease, or a combination of these. In some embodiments, the disease is a cancer.

After obtaining or providing the cell-free nucleic acid molecules, any of a number of different library preparation procedures for preparing nucleic acid molecules for sequencing may be performed on the cell-free nucleic acid molecules. Cell-free nucleic acid molecules may be processed before sequencing with one or more reagents (e.g., enzymes, adapters, tags (e.g. barcodes), probes, etc.). Tagged molecules may then be used in a downstream application, such as a sequencing reaction by which individual molecules may be tracked.

In some embodiments, the methods may further comprise an enrichment step prior to sequencing, whereby regions of the tagged molecules are selectively or non-selectively enriched.

Once sequencing data of the cell-free nucleic acid molecules is collected, one or more bioinformatics processes may be applied to the sequence data to detect an alignment error (e.g., a false positive sequence read), such as one caused by presence of a PPG, and suppressing or eliminating the alignment error when providing results of a genetic sequencing test. Such processes may include, but are not limited to identifying germline and somatic gene fusion sequence reads, identifying somatic single nucleotide variants (SNV) and/or insertions or deletions (indels) within a sequence read, determining alignment errors within a region of gene fusion breakpoints (e.g., intragenic or intergenic), applying a filter to remove alignment errors based on predetermined criteria from the sequence reads or from the final set of detected variants, and identifying true genetic variants from the filtered sequence reads.

In some cases, sequence reads generated from a sequencing reaction can be aligned to a reference sequence for carrying out bioinformatics analysis. In various aspects of bioinformatics analysis, one or more thresholds may be set to ensure quality. For example, an alignment threshold may be set such that only highly similar sequence reads (e.g., with 10 or less mismatches between a reference sequence and sequence reads) are mapped to a reference sequence. In some cases, sequence reads may be removed that cannot pass a quality threshold, e.g. based on chromatograms of sequence reads. In some cases, copy numbers or amounts of a given sequence may be quantified based on the number of sequence reads mapping or aligning to the given sequence. In some cases, over-representation of sequence(s) may be determined by comparing copy numbers or amounts of different sequences among all sequence reads.

In certain embodiments, a sample may be contacted with a sufficient number of adapters that there is a low probability (e.g., <1%) that any two copies of the same nucleic acid receive the same combination of adapter molecular barcodes from the adapters linked at one end or both ends. The use of adapters in this manner may permit grouping of sequence reads with the same start and stop points that are aligned (or mapped) to a reference sequence and linked to the same combination of barcodes into families of reads generated from the same original molecule. Such a family may represent sequences of amplification products of a nucleic acid in the sample before amplification.

In some embodiments, sequences of family members can be compiled to derive consensus nucleotide(s) or a complete consensus sequence for a nucleic acid molecule in the original sample, as modified by blunt ending and adapter attachment. In other words, the nucleotide occupying a specified position of a nucleic acid in the sample may be determined to be the consensus of nucleotides occupying that corresponding position in family member sequences. A consensus nucleotide can be determined by methods such as voting or confidence score, to name two non-limiting, exemplary methods. Families can include sequences of one or both strands of a double-stranded nucleic acid. If members of a family include sequences of both strands from a double-stranded nucleic acid, sequences of one strand are converted to their complement for purposes of compiling all sequences to derive consensus nucleotide(s) or sequences. Some families may include only a single member sequence. In this case, this sequence can be taken as the sequence of a nucleic acid in the sample before amplification. Alternatively, families with only a single member sequence can be eliminated from subsequent analysis.

The reference sequence may be one or more known sequences, e.g., a known whole or partial genome sequence from a given subject, such as a whole genome sequence of a human subject. The reference sequence can be hG19. The sequenced nucleic acids can represent sequences determined directly for a nucleic acid in a sample, or a consensus of sequences of amplification products of such a nucleic acid, as described above. A comparison can be performed at one or more designated positions on a reference sequence. A subset of sequenced nucleic acids can be identified including a position corresponding with a designated position of the reference sequence when the respective sequences are maximally aligned. Within such a subset it can be determined which, if any, sequenced nucleic acids include a nucleotide variation at the designated position, and optionally which if any, include a reference nucleotide (i.e., same as in the reference sequence). If the number of sequenced nucleic acids in the subset including a nucleotide variant exceeds a threshold, then a variant nucleotide can be called at the designated position. The threshold can be a simple number, such as at least 1, 2, 3, 4, 5, 6, 7, 8, 9, or 10 sequenced nucleic acid within the subset including the nucleotide variant or it can be a ratio, such as a least 0.5, 1, 2, 3, 4, 5, 10, 15, or 20 percent of sequenced nucleic acids within the subset include the nucleotide variant, among other possibilities. The comparison can be repeated for any designated position of interest in the reference sequence. Sometimes a comparison can be performed for designated positions occupying at least 20, 100, 200, or 300 contiguous positions on a reference sequence, e.g., 20-500, or 50-300 contiguous positions.

FIG. 1 shows an embodiment of a method for detecting and suppressing alignment errors. In general, the method may use a variant caller and/or a fusion caller to identify a set of potential genetic variants according to a predetermined set of specified thresholds. For example, a variant caller may be used to identify a set of somatic SNV or indel variants according to specified thresholds, and a fusion caller may be used to identify a set of germline and somatic intragenic (within-gene) gene fusions according to specific thresholds. Such a set of potential genetic variants may include one or more alignment errors in which variants may be incorrectly assigned to a gene when they originate from the presence of a processed pseudogene (thereby causing the detection of false positive genetic variants). Such alignment errors may be detected and suppressed during a variant calling process, such as, for example, by filtering or removing such detected alignment errors from identification or further analysis as potential genetic variants.

Figure 2:
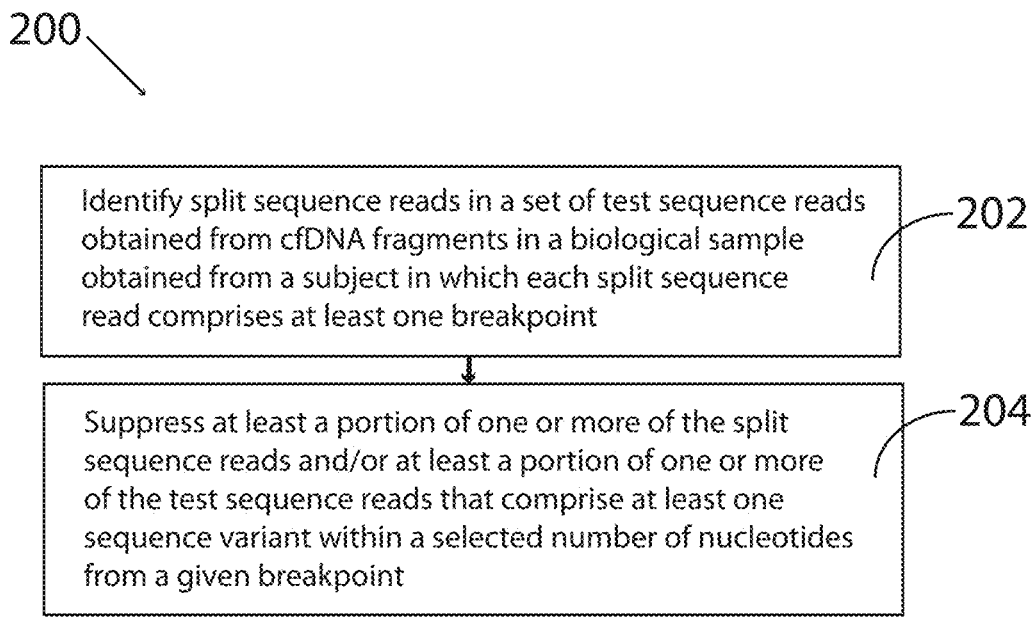
FIG. 2 is a flow chart that schematically depicts exemplary method steps of producing a filtered sequence information data set according to some embodiments of the disclosure.
Figure 3:
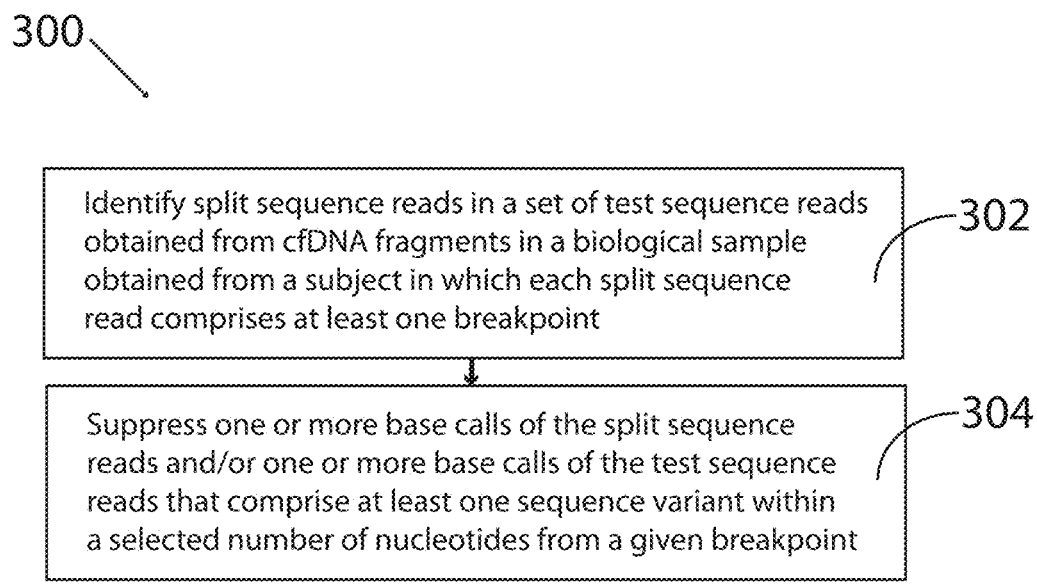
FIG. 3 is a flow chart that schematically depicts exemplary method steps of producing a filtered sequence information data set according to some embodiments of the disclosure.
Figure 4:
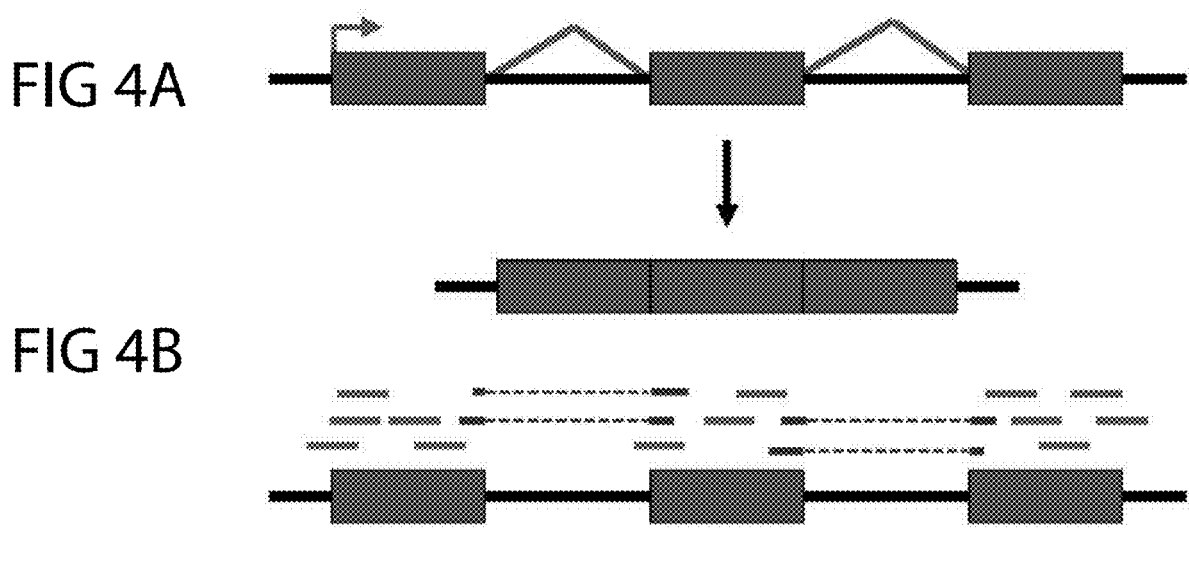
FIG. 4A is a diagram showing a process by which processed pseudogenes are created. Non-specific reverse transcriptase machinery present in human LINE elements creates and integrates a DNA copy of a processed (i.e., intronless) mRNA into the genome.
FIG. 4B is a diagram showing how reads originating from the pseudogene may map uniquely to the original gene because sample-specific PPGs are not in the human genome assembly (e.g. hG19). However, the presence of pseudogenes may be revealed by a presence of split reads originating from PPG fragments spanning the intron-exon boundaries.

To further illustrate aspects of the methods disclosed herein, FIGS. 2 and 3 provide flow charts that schematically depict exemplary method steps for producing filtered sequence information data sets at least partially using a computer. Any of the methods disclosed herein are optionally at least partially implemented or embodied in systems or computer readable media, which are also described further herein. As shown, in FIGS. 2 and 3, methods 200 and 300 both include identifying split sequence reads in a set of test sequence reads obtained from cfDNA molecules or fragments in a biological sample obtained from a subject in which each split sequence read comprises at least one breakpoint in steps 202 and 302, respectively. Typically, methods 200 and 300 each include receiving (e.g., via an electronic communication network or other communication or storage medium) test sequence information comprising the test sequence reads from the cfDNA molecules in the biological sample obtained from the subject prior to steps 202 and 302. In some embodiments, methods 200 and 300 each include sequencing the cfDNA fragments in the biological sample obtained from the subject to produce the set of test sequence reads (i.e., test sequence information) prior to steps 202 and 302.

Split sequence reads or alignment errors are optionally identified in test sequence information obtained from a sample using any one or more of a variety of techniques. In some embodiments, split sequence reads are identified by identifying test sequence reads in a set of test sequence information that only partially aligns with a given set of reference sequence information. For example, a split sequence read typically includes at least a first sub-sequence that maps to a first region of a given reference genomic sequence and at least a second sub-sequence that maps to a second region of the given reference genomic sequence in which the first and second regions of the given reference genomic sequence are non-contiguous or non-adjacent with one another. In some of these embodiments, the methods include identifying a first sub-sequence adjacent to a first breakpoint that maps to a first genetic locus (e.g., an intragenic or intergenic locus of the given reference genomic sequence) and identifying a second sub-sequence adjacent to a second breakpoint that maps to a second, distinct genetic locus (e.g., a non-contiguous intragenic or non-contiguous intergenic locus of the given reference genomic sequence). In these embodiments, the first breakpoint and the second breakpoint form a breakpoint pair.

In other exemplary embodiments, a given split sequence read or alignment error is identified by identifying an increased coverage of genomic regions (e.g., coding sequences (CDSs), etc.) observed in test sequence information relative to reference sequence information that lacks split sequence reads comprising the genomic regions. In some embodiments, a suspected split sequence or gene fusion (e.g., a processed pseudogene (PPG)) is not called as such unless at least two (e.g., 2, 3, 4, 5, 6, 7, 8, 9, 10, or more) split sequence reads that each include at least one identical breakpoint, but that otherwise differ from one another in a given property, such as in terms of length, which may indicate that the split sequence reads originate from different cfDNA fragments in a given sample. This typically increases the confidence level that a true split sequence or gene fusion is being observed in a given sample. Additional details regarding identifying split sequence read and gene fusions, which are optionally adapted for use with the methods and related aspects of the present disclosure, are provided in, for example, WO 2017/062970 and WO 2018/213814, which are each incorporated by reference.

As also shown, in FIGS. 2 and 3, method 200 includes suppressing, in the set of test sequence reads, at least a portion of one or more of the split sequence reads (e.g., at least a portion of a given read(s) and/or entire read(s)) and/or at least a portion of one or more of the test sequence reads (e.g., at least a portion of a given read(s) and/or entire read(s)) that comprise at least one sequence variant within a selected number of nucleotides from a given breakpoint in step 204, whereas method 300 includes suppressing, in the set of test sequence reads, one or more base calls of the split sequence reads and/or one or more base calls of the test sequence reads that comprise at least one sequence variant within a selected number of nucleotides from a given breakpoint in step 304 to produce filtered sequence information data sets. Sequence reads (or portions thereof) and/or base calls are typically "suppressed" by removing that information from the given data set or by simply not using that information in a given application of the data set. In some exemplary embodiments, as described herein, suppressed split sequence reads comprise at least a portion of a processed pseudogene (PPG).

In some embodiments, a sequence variant within a selected number of nucleotides of a given breakpoint includes a mutant allele fraction (MAF) that is less than or equal to an MAF of the breakpoint in the biological sample. Although other numbers are optionally used, the selected number of nucleotides from the given breakpoint typically comprises about 1, 2, 3, 4, 5, 6, 7, 8, 9, 19, 11, 12, 13, 14, 15, 16, 17, 18, 19, 20, or more nucleotides. In other embodiments, the number of nucleotides from the given breakpoint may comprise fewer than 100, 50, 20, 15, 10, 8, 6, 4, or 2 nucleotides. In addition, the selected number of nucleotides from the given breakpoint is located 5' and/or 3' to the given breakpoint (i.e., on either side or on both sides of the given breakpoint). As described herein, various types of sequence variants are optionally used in performing the methods of the present disclosure. In some of these embodiments, for example, the sequence variant comprises a single nucleotide variant (SNV) and/or an insertion or deletion (indel). In certain embodiments, the methods include suppressing one or more additional test sequence reads or portions thereof that comprise one or more sequence variants that are not within the selected number of nucleotides from a given breakpoint when the additional test sequence reads align with at least a portion of one or more gene sequences selected from the group consisting of: SMAD4, GNAS, TP53, RAF1, CDK4, TYR03, MAPK1, STK11, CCND1, HRAS, MET, MYC, and NRAS.

The filtered sequence information data sets produced using the methods disclosed herein can be used in a wide variety of applications. Typically, they are used to facilitate identifying sequence variants of clinical significance in a test sample obtained from a subject to determine whether the subject has a given disease, disorder, or condition. In certain embodiments, once a particular disease, disorder, or condition has been so diagnosed, the methods further include administering one or more therapies to the subject to treat that disease, disorder, or condition in the subject, as described further herein.

Gene fusions may be identified from a sample of a subject by using liquid biopsy assays to identify somatic genomic alterations in cell-free DNA (e.g., which includes circulating tumor DNA, ctDNA). Such assays may comprise sequencing cell-free DNA molecules to produce sequence reads and analyzing the sequence reads using a panel of gene markers (e.g., ALK, FGFR2, FGFR3, NTRK1, RET, and ROS1).

PPGs may be germline or somatic in origin, and may be identified by analyzing sequence read coverage data across a genome at one or more genetic loci. For example, PPGs may be found in locations where alignment artefacts are observed across exon-exon junctions. The presence of a PPG may be revealed by a presence of multiple soft-clipped reads (i.e., those reads where part of the sequence read is not aligned with the reference sequence) lacking intronic sequence, or by a discontinuity of coverage at an intron-exon boundary. PPGs may be derived from the exonic sequences of, for example, SMAD4, GNAS, TP53, RAF1, CDK4, TYRO3, MAPK1, STK11, CCND1, HRAS, MET, MYC, and NRAS.

One or more criteria may be used to identify potential alignment errors. For example, out of a set of sequence reads corresponding to gene fusions (gene fusion reads) that include an intragenic fusion breakpoint, potential alignment errors may be identified from a subset of the reads overlapping the gene fusion that comprise genetic variants within a region comprising the intragenic fusion breakpoint. The region may comprise 20 or fewer nucleotides (e.g., about 20, 15, 10, 8, 6, 4, or 2 nucleotides) adjacent to the intragenic fusion breakpoint. The set of the gene fusion reads may correspond to one or more processed pseudogenes (PPGs), such as sample-specific PPGs (which are specific to a given sample or subject and are generally not found in a reference human genome, such as hG19). The genetic variants may comprise a single nucleotide variant (SNV) or an insertion or deletion (indel). For example, the SNV may be located at an intron-exon boundary or located within a gene coding sequence (CDS).

As another example, out of a set of sequence reads corresponding to gene fusions (gene fusion reads), potential alignment errors may be identified from a subset of the gene fusion reads being detected in the SMAD4, TYRO3, and/or RAF1 genes.

Potential alignment errors that have been identified may be suppressed when detecting a true genetic variant (e.g., from cell-free DNA molecules from a sample of a subject). For example, at least a portion of such identified potential alignment errors may be filtered out from the set of gene fusion reads to produce filtered sequence reads. Such filtered sequence reads may then be processed or analyzed to detect true genetic variants (e.g., not caused by false positive variants as a consequence of a presence of PPGs) as compared to a reference sequence, thereby advantageously decreasing a rate of false positive detection of variants. Consequently, variants may be identified from analysis of a sample from a subject with greater accuracy, sensitivity, specificity, positive predictive value (PPV), negative predictive value (NPV), or area-under-the-curve (AUC).

In some cases, a portion of the detected alignment errors is filtered out based on the detected alignment errors having a mutant allele fraction (MAF) in the sample which is less than or equal to a MAF of the intragenic fusion corresponding to the intragenic fusion breakpoint in the sample. Because fusion-mediated errors may be found in fusion-spanning reads, the false positive alignment errors may not have an MAF in the sample larger than the MAF of the intragenic fusion corresponding to the intragenic fusion breakpoint in the sample.

In some cases, a portion of the detected alignment errors is filtered out based on the gene fusion reads that comprise genetic variants not belonging to a pre-defined set of clinically actionable variants. Such "whitelisted" variants may be found in various databases of variants whose presence in a sample of a subject have been shown to correlate with or be indicative of a disease or disorder (e.g., cancer) in the subject. Such databases of variants may include, for example, the Catalogue of Somatic Mutations in Cancer (COSMIC), The Cancer Genome Atlas (TCGA), and the Exome Aggregation Consortium (ExAC). A pre-defined set of such catalogued variants may be designated for further bioinformatics analysis due to their relevance to clinical decision-making (e.g., diagnosis, prognosis, treatment selection, targeted treatment, treatment monitoring, monitoring for recurrence, etc.). Such a pre-defined set may be determined based on, for example, analysis of clinical samples (e.g., of patient cohorts with known presence or absence of a disease or disorder) as well as annotation information from public databases and clinical literature.

After identifying and suppressing alignment errors, the filtered set of sequence reads may be analyzed to detect true genetic variants as compared to a reference sequence.

The disclosure further provides that the method steps disclosed herein are optionally adapted for performance using systems and/or computer readable media disclosed herein. In certain aspects, a system may comprise a controller comprising, or capable of accessing, computer readable media comprising non-transitory computer-executable instructions, which, when executed by at least one electronic processor performs at least one of the methods described herein.

In some embodiments, the sequencer is a DNA sequencer. In some embodiments, the sequencer is designed to perform high-throughput sequencing, such as next generation sequencing. In some embodiments, the system comprises adapter tagged cfDNA molecules in the sequencers. In some embodiments, the adapter tagged cfDNA molecules are sourced from one subject or a plurality of subjects. In some embodiments, the cfDNA molecules from the sample bear unique or non-unique barcodes.

In some embodiments, the method implemented by the computer processor further comprises grouping the sequence reads into families, each of the families comprising sequence reads comprising the same barcodes and having the same start and stop positions, whereby each of the families comprises sequence reads amplified from the same original cfDNA molecule.

In some embodiments, the methods and systems described herein utilize a digital processing device. In further embodiments, the digital processing device includes one or more hardware central processing units (CPUs) or general purpose graphics processing units (GPGPUs) that carry out the device's functions. In still further embodiments, the digital processing device further comprises an operating system configured to perform executable instructions. In some embodiments, the digital processing device is optionally connected to a computer network. In further embodiments, the digital processing device is optionally connected to the Internet such that it accesses the World Wide Web. In still further embodiments, the digital processing device is optionally connected to a cloud computing infrastructure. In other embodiments, the digital processing device is optionally connected to an intranet. In other embodiments, the digital processing device is optionally connected to a data storage device. In accordance with the description herein, suitable digital processing devices include, by way of non-limiting examples, server computers, desktop computers, laptop computers, notebook computers, handheld computers, Internet appliances, mobile smartphones, and tablet computers.

In some embodiments, the digital processing device includes an operating system configured to perform executable instructions. The operating system is, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®.

In some embodiments, the device includes a storage and/or memory device. The storage and/or memory device is one or more physical apparatuses used to store data or programs on a temporary or permanent basis. In some embodiments, the device is volatile memory and requires power to maintain stored information. In some embodiments, the device is non-volatile memory and retains stored information when the digital processing device is not powered. In further embodiments, the non-volatile memory comprises flash memory. In some embodiments, the non-volatile memory comprises dynamic random-access memory (DRAM). In some embodiments, the non-volatile memory comprises ferroelectric random access memory (FRAM). In some embodiments, the non-volatile memory comprises phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device includes an electronic display to send visual information to a user. In some embodiments, the display is a liquid crystal display (LCD). In further embodiments, the display is a thin film transistor liquid crystal display (TFT-LCD). In some embodiments, the display is an organic light emitting diode (OLED) display. In various further embodiments, on OLED display is a passive-matrix OLED (PMOLED) or active-matrix OLED (AMOLED) display. In some embodiments, the display is a plasma display. In other embodiments, the display is a video projector. In yet other embodiments, the display is a head-mounted display in communication with the digital processing device, such as a VR headset. In further embodiments, suitable VR headsets include, by way of non-limiting examples, HTC Vive, Oculus Rift, Samsung Gear VR, Microsoft HoloLens, Razer OSVR, FOVE VR, Zeiss VR One, Avegant Glyph, Freefly VR headset, and the like. In still further embodiments, the display is a combination of devices such as those disclosed herein.

In some embodiments, the digital processing device includes an input device to receive information from a user. In some embodiments, the input device is a keyboard. In some embodiments, the input device is a pointing device including, by way of non-limiting examples, a mouse, trackball, track pad, joystick, game controller, or stylus. In some embodiments, the input device is a touch screen or a multi-touch screen. In other embodiments, the input device is a microphone to capture voice or other sound input. In other embodiments, the input device is a video camera or other sensor to capture motion or visual input. In further embodiments, the input device is a Kinect, Leap Motion, or the like. In still further embodiments, the input device is a combination of devices such as those disclosed herein.

In some aspects, the present disclosure provides a system, comprising a controller comprising, or capable of accessing, computer readable media comprising non-transitory computer-executable instructions which, when executed by at least one electronic processor, perform a method provided herein.

Figure 5:
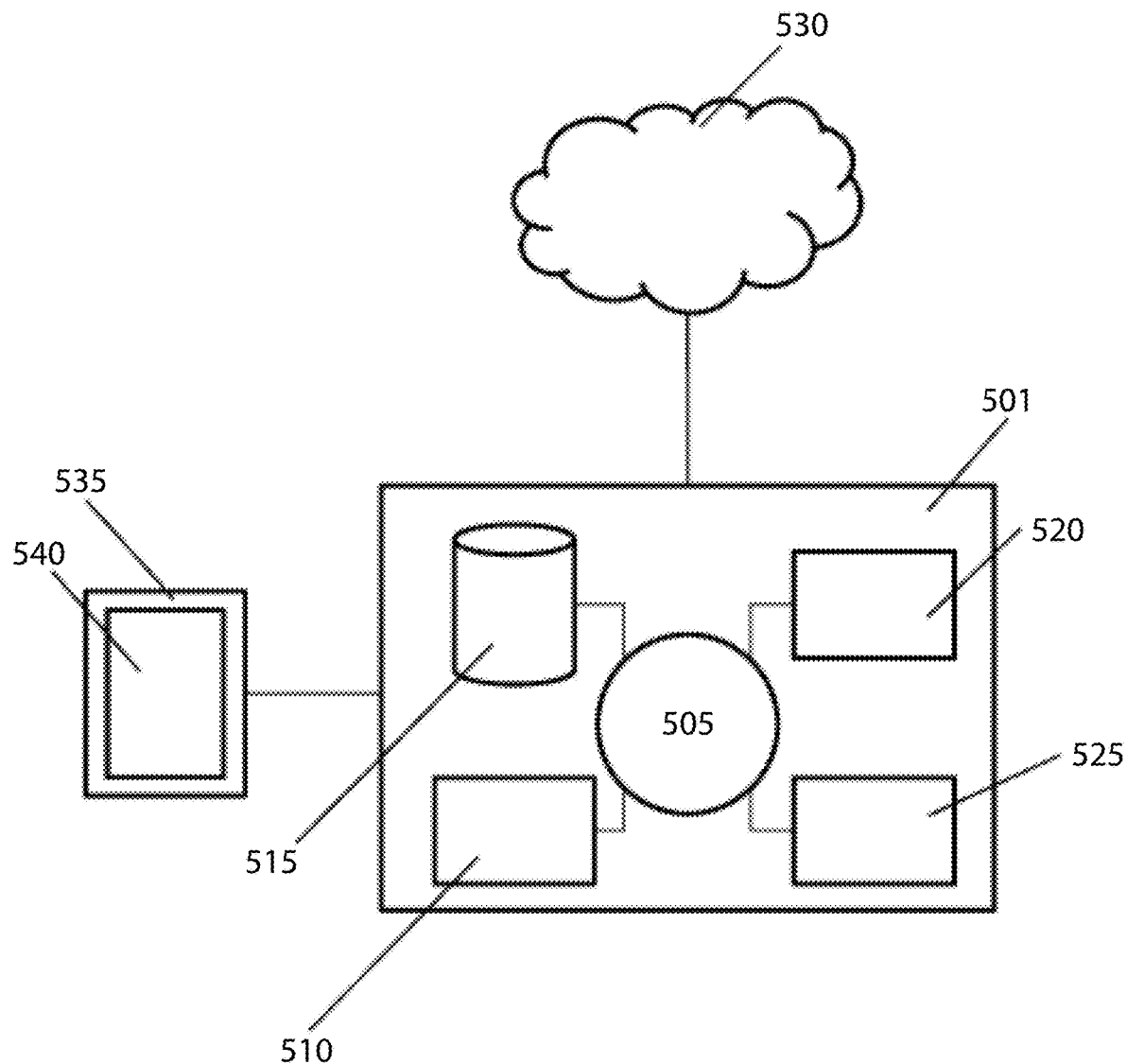
FIG. 5 is a diagram showing a computer system that is programmed or otherwise configured to implement methods provided herein.

FIG. 5 shows a computer system 501 that is programmed or otherwise configured to implement methods provided herein.

The computer system 501 may be programmed or otherwise configured to implement methods for detecting and/or suppressing alignment errors in genetic sequence reads. The computer system 501 can regulate various aspects of the present disclosure, such as, for example, (a) sequencing cell-free nucleic acid molecules in a biological sample to generate genetic sequence reads; (b) aligning genetic sequence reads to a reference sequence to produce aligned sequence reads; (c) identifying, from the aligned sequence reads, a set of gene fusion reads that comprise an intragenic fusion breakpoint; (d) detecting an alignment error by identifying a subset of one or more of the gene fusion reads that comprise genetic variants within a region comprising the intragenic fusion breakpoint, wherein the region comprises one or more nucleotides adjacent to the intragenic fusion breakpoint; (e) filtering out at least a portion of the detected alignment errors in the subset of the gene fusion reads to produce filtered sequence reads; and (f) detecting filtered sequence reads that include a true genetic variant as compared to the reference sequence. The computer system 501 can be an electronic device of a user or a computer system that is remotely located with respect to the electronic device. The electronic device can be a mobile electronic device.

The computer system 501 includes a central processing unit (CPU, also "processor" and "computer processor" herein) 505, which can be a single core or multi core processor, or a plurality of processors for parallel processing. The computer system 501 also includes memory or memory location 510 (e.g., random-access memory, read-only memory, flash memory), electronic storage unit 515 (e.g., hard disk), communication interface 520 (e.g., network adapter) for communicating with one or more other systems, and peripheral devices 525, such as cache, other memory, data storage and/or electronic display adapters. The memory 510, storage unit 515, interface 520 and peripheral devices 525 are in communication with the CPU 505 through a communication bus (solid lines), such as a motherboard. The storage unit 515 can be a data storage unit (or data repository) for storing data. The computer system 501 can be operatively coupled to a computer network ("network") 530 with the aid of the communication interface 520. The network 530 can be the Internet, an internet and/or extranet, or an intranet and/or extranet that is in communication with the Internet. The network 530 in some cases is a telecommunication and/or data network. The network 530 can include one or more computer servers, which can enable distributed computing, such as cloud computing. The network 530, in some cases with the aid of the computer system 501, can implement a peer-to-peer network, which may enable devices coupled to the computer system 501 to behave as a client or a server.

The CPU 505 can execute a sequence of machine-readable instructions, which can be embodied in a program or software. The instructions may be stored in a memory location, such as the memory 510. The instructions can be directed to the CPU 505, which can subsequently program or otherwise configure the CPU 505 to implement methods of the present disclosure. Examples of operations performed by the CPU 505 can include fetch, decode, execute, and writeback.

The CPU 505 can be part of a circuit, such as an integrated circuit. One or more other components of the system 501 can be included in the circuit. In some cases, the circuit is an application specific integrated circuit (ASIC).

The storage unit 515 can store files, such as drivers, libraries and saved programs. The storage unit 515 can store user data, e.g., user preferences and user programs. The computer system 501 in some cases can include one or more additional data storage units that are external to the computer system 501, such as located on a remote server that is in communication with the computer system 501 through an intranet or the Internet.

The computer system 501 can communicate with one or more remote computer systems through the network 530. For instance, the computer system 501 can communicate with a remote computer system of a user. Examples of remote computer systems include personal computers (e.g., portable PC), slate or tablet PC's (e.g., Apple® iPad, Samsung® Galaxy Tab), telephones, Smart phones (e.g., Apple® iPhone, Android-enabled device, Blackberry®), or personal digital assistants. The user can access the computer system 501 via the network 530.

Methods as described herein can be implemented by way of machine (e.g., computer processor) executable code stored on an electronic storage location of the computer system 501, such as, for example, on the memory 510 or electronic storage unit 515. The machine executable or machine-readable code can be provided in the form of software. During use, the code can be executed by the processor 505. In some cases, the code can be retrieved from the storage unit 515 and stored on the memory 510 for ready access by the processor 505. In some situations, the electronic storage unit 515 can be precluded, and machine-executable instructions are stored on memory 510.

The code can be pre-compiled and configured for use with a machine having a processor adapted to execute the code, or can be compiled during runtime. The code can be supplied in a programming language that can be selected to enable the code to execute in a pre-compiled or as-compiled fashion.

Aspects of the systems and methods provided herein, such as the computer system 501, can be embodied in programming. Various aspects of the technology may be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer into the computer platform of an application server. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to non-transitory, tangible "storage" media, terms such as computer or machine "readable medium" refer to any medium that participates in providing instructions to a processor for execution.

Hence, a machine-readable medium, such as computer-executable code, may take many forms, including but not limited to, a tangible storage medium, a carrier wave medium or physical transmission medium. Non-volatile storage media include, for example, optical or magnetic disks, such as any of the storage devices in any computer(s) or the like, such as may be used to implement the databases, etc. shown in the drawings. Volatile storage media include dynamic memory, such as main memory of such a computer platform. Tangible transmission media include coaxial cables; copper wire and fiber optics, including the wires that comprise a bus within a computer system. Carrier-wave transmission media may take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a processor for execution.

The computer system 501 can include or be in communication with an electronic display 535 that comprises a user interface (UI) 540. Examples of UIs include, without limitation, a graphical user interface (GUI) and web-based user interface.

Methods and systems of the present disclosure can be implemented by way of one or more algorithms. An algorithm can be implemented by way of software upon execution by the central processing unit 505. The algorithm can, for example, (a) sequence cell-free nucleic acid molecules in a biological sample to generate genetic sequence reads; (b) align genetic sequence reads to a reference sequence to produce aligned sequence reads; (c) identify, from the aligned sequence reads, a set of gene fusion reads that comprise an intragenic fusion breakpoint; (d) detect an alignment error by identifying a subset of one or more of the gene fusion reads that comprise genetic variants within a region comprising the intragenic fusion breakpoint, wherein the region comprises one or more nucleotides adjacent to the intragenic fusion breakpoint; (e) filter out at least a portion of the detected alignment errors in the subset of the gene fusion reads to produce filtered sequence reads; and (f) detect filtered sequence reads that include a true genetic variant as compared to the reference sequence.

II. General Features of the Methods

A. Samples

A sample can be any biological sample isolated from a subject. Samples can include body tissues, such as known or suspected solid tumors, whole blood, platelets, serum, plasma, stool, red blood cells, white blood cells or leucocytes, endothelial cells, tissue biopsies, cerebrospinal fluid synovial fluid, lymphatic fluid, ascites fluid, interstitial or extracellular fluid, the fluid in spaces between cells, including gingival crevicular fluid, bone marrow, pleural effusions, cerebrospinal fluid, saliva, mucous, sputum, semen, sweat, urine. Samples are preferably body fluids, particularly blood and fractions thereof, and urine. Samples may also include nucleic acids shed from tumors, e.g., circulating tumor DNA (ctDNA). The nucleic acids can include DNA and RNA and can be in double- and single-stranded forms. A sample can be in the form originally isolated from a subject or can have been subjected to further processing to remove or add components, such as cells, enrich for one component relative to another, or convert one form of nucleic acid to another, such as RNA to DNA or single-stranded nucleic acids to double-stranded. Thus, for example, a body fluid for analysis is plasma or serum containing cell-free nucleic acids, e.g., cell-free DNA (cfDNA).

The volume of plasma can depend on the desired read depth for sequenced regions. Exemplary volumes are 0.4-40 ml, 5-20 ml, and 10-20 ml. For example, the volume can be 0.5 ml, 1 mL, 5 ml, 10 ml, 20 ml, 30 ml, or 40 ml. A volume of sampled plasma may be 5 to 20 ml.

The sample can comprise various amounts of nucleic acid that contains genome equivalents. For example, a sample of about 30 ng DNA can contain about 10,000 ($10^4$) haploid human genome equivalents and, in the case of cfDNA, about 200 billion ($2\times10^{11}$) individual polynucleotide molecules. Similarly, a sample of about 100 ng of DNA can contain about 30,000 haploid human genome equivalents and, in the case of cfDNA, about 600 billion individual molecules.

A sample can comprise nucleic acids from different sources, e.g., cell free or from a foreign object. A sample can comprise nucleic acids carrying mutations. For example, a sample can comprise DNA carrying germline mutations and/or somatic mutations. A sample can comprise DNA carrying cancer-associated mutations (e.g., cancer-associated somatic mutations).

Exemplary amounts of cell-free nucleic acids in a sample before amplification range from about 1 femtogram (fg) to about 1 microgram (ug), e.g., 1 picogram (pg) to 200 nanograms (ng), 1 ng to 100 ng, 10 ng to 1000 ng. For example, the amount can be up to about 600 ng, up to about 500 ng, up to about 400 ng, up to about 300 ng, up to about 200 ng, up to about 100 ng, up to about 50 ng, or up to about 20 ng of cell-free nucleic acid molecules. The amount can be at least 1 fg, at least 10 fg, at least 100 fg, at least 1 pg, at least 10 pg, at least 100 pg, at least 1 ng, at least 10 ng, at least 100 ng, at least 150 ng, or at least 200 ng of cell-free nucleic acid molecules. The amount can be up to 1 femtogram (fg), 10 fg, 100 fg, 1 picogram (pg), 10 pg, 100 pg, 1 ng, 10 ng, 100 ng, 150 ng, or 200 ng of cell-free nucleic acid molecules. The method can comprise obtaining 1 femtogram (fg) to 200 ng.

In certain embodiments, the amount of cell-free nucleic acids in the sample is between about 5 ng and 300 ng.

Cell-free nucleic acids have an exemplary size distribution of about 100-500 nucleotides, with molecules of 110 to about 230 nucleotides representing about 90% of molecules, with a mode of about 168 nucleotides and a second minor peak in a range between 240 to 440 nucleotides. Cell-free nucleic acids can be about 160 to about 180 nucleotides, or about 320 to about 360 nucleotides, or about 440 to about 480 nucleotides.

Cell-free nucleic acids can be isolated from bodily fluids through a partitioning step in which cell-free nucleic acids, as found in solution, are separated from intact cells and other non-soluble components of the bodily fluid. Partitioning may include techniques such as centrifugation or filtration. Alternatively, cells in bodily fluids can be lysed and cell-free and cellular nucleic acids processed together. Generally, after addition of buffers and wash steps, cell-free nucleic acids can be precipitated with an alcohol. Further clean up steps may be used such as silica based columns to remove contaminants or salts. Non-specific bulk carrier nucleic acids, for example, may be added throughout the reaction to optimize certain aspects of the procedure such as yield. After such processing, samples can include various forms of nucleic acid including double-stranded DNA, single stranded DNA and single stranded RNA. Optionally, single stranded DNA and RNA can be converted to double-stranded forms so they are included in subsequent processing and analysis steps.

B. Tags

Tags providing sample indexes and/or molecular barcodes can be incorporated into or otherwise joined to adapters by chemical synthesis, ligation, overlap extension PCR among other methods. Generally, assignment of unique or non-unique molecular barcodes in reactions follows methods and systems described by US patent applications 20010053519, 20110160078, and U.S. Pat. Nos. 6,582,908, 7,537,898, and 9,598,731.

Tags can be linked to sample nucleic acids randomly or non-randomly. In some cases, they are introduced at an expected ratio. The collection of barcodes can be unique, e.g., all the barcodes have the same nucleotide sequence. The collection of barcodes can be non-unique, e.g., some of the barcodes have the same nucleotide sequence, and some of the barcodes have different nucleotide sequence. For example, the identifiers may be loaded so that more than 1, 2, 3, 4, 5, 6, 7, 8, 9, 10, 20, 50, 100, 500, 1000, 5000, 10000, 50,000, 100,000, 500,000, 1,000,000, 10,000,000, 50,000,000, or 1,000,000,000 identifiers are loaded per genome sample. In some cases, the identifiers may be loaded so that less than 2, 3, 4, 5, 6, 7, 8, 9, 10, 20, 50, 100, 500, 1000, 5000, 10000, 50,000, 100,000, 500,000, 1,000,000, 10,000,000, 50,000,000, or 1,000,000,000 identifiers are loaded per genome sample. In some cases, the average number of identifiers loaded per sample genome is less than, or greater than, about 1, 2, 3, 4, 5, 6, 7, 8, 9, 10, 20, 50, 100, 500, 1000, 5000, 10000, 50,000, 100,000, 500,000, 1,000,000, 10,000,000, 50,000,000, or 1,000,000,000 identifiers per genome sample.

A preferred format uses 20-50 different tags, ligated to both ends of a target molecule creating 20-50×20-50 tags.

Such numbers of tags are sufficient that different molecules having the same start and stop points have a high probability (e.g., at least 94%, 99.5%, 99.99%, 99.999%) of receiving different combinations of tags.

In some cases, identifiers may be predetermined or random or semi-random sequence oligonucleotides. In other cases, a plurality of barcodes may be used such that barcodes are not necessarily unique to one another in the plurality. In this example, barcodes may be attached (e.g., by ligation or PCR amplification) to individual molecules such that the combination of the barcode and the sequence it may be attached to creates a unique sequence that may be individually tracked. As described herein, detection of non-unique molecular barcodes in combination with sequence data of beginning (start) and end (stop) portions of sequence reads that map to a reference sequence or genome may allow assignment of a unique identity to a particular molecule. The length, or number of base pairs, of an individual sequence read may also be used to assign a unique identity to such a molecule. As described herein, fragments from a single strand of nucleic acid having been assigned a unique identity, may thereby permit subsequent identification of fragments from the parent strand, and/or a complementary strand.

One or more amplifications can be applied to introduce molecular barcodes and/or sample indexes to a nucleic acid molecule using conventional nucleic acid amplification methods. The amplification can be conducted in one or more reaction mixtures. Molecular barcodes and sample indexes can be introduced simultaneously, or in any sequential order. Molecular barcodes and sample indexes can be introduced prior to and/or after sequence capturing (e.g. enrichment). In some embodiments, only the molecule tags are introduced prior to probe capturing while the sample indexes/tags are introduced after sequence capturing. In some cases, both the molecular barcodes and the sample indexes are introduced prior to probe capturing. In some cases, the sample indexes are introduced after sequence capturing. Usually, sequence capturing involves introducing a single-stranded nucleic acid molecule complementary to a targeted sequence. Typically, the amplifications generate a plurality of non-uniquely or uniquely tagged nucleic acid amplicons with molecular barcodes and sample indexes at a size ranging from 200 nucleotides (nt) to 700 nt, 250 nt to 350 nt, or 320 nt to 550 nt. In some embodiments, the amplicons have a size of about 300 nt. In some embodiments, the amplicons have a size of about 500 nt.

C. Amplification

Sample nucleic acids flanked by adapters can be amplified by PCR and other amplification methods typically primed from primers binding to primer binding sites in adapters flanking a nucleic acid molecule to be amplified. Amplification methods can involve cycles of extension, denaturation and annealing resulting from thermocycling or can be isothermal as in transcription mediated amplification. Other amplification methods include the ligase chain reaction, strand displacement amplification, nucleic acid sequence based amplification, and self-sustained sequence based replication.

D. Enrichment

Sequences can be enriched prior to sequencing. Enrichment can be performed for specific target regions or non-specifically ("target sequences"). In some embodiments, targeted regions of interest may be enriched with capture probes ("baits") selected for one or more bait set panels using a differential tiling and capture scheme. A differential tiling and capture scheme uses bait sets of different relative concentrations to differentially tile (e.g., at different "resolutions") across genomic regions associated with baits, subject to a set of constraints (e.g., sequencer constraints such as sequencing load, utility of each bait, etc.), and capture them at a desired level for downstream sequencing. In some embodiments, biotin-labeled beads with probes to one or more regions of interest can be used to capture target sequences, optionally followed by amplification of those regions, to enrich for the regions of interest.

Sequence capture typically involves the use of oligonucleotide probes that hybridize to the target sequence. A probe set strategy can involve tiling the probes across a region of interest. Such probes can be, e.g., about 60 to 120 bases long. The set can have a depth of about 2×, 3×, 4×, 5×, 6×, 8×, 9×, 10×, 15×, 20×, 50×, or more. The effectiveness of sequence capture depends, in part, on the length of the sequence in the target molecule that is complementary (or nearly complementary) to the sequence of the probe.

E. Sequencing

Sample nucleic acids flanked by adapters with or without prior amplification can be subject to sequencing. Sequencing methods include, for example, Sanger sequencing, high-throughput sequencing, pyrosequencing, sequencing-by-synthesis, single-molecule sequencing, nanopore sequencing, semiconductor sequencing, sequencing-by-ligation, sequencing-by-hybridization, RNA-Seq (Illumina), Digital Gene Expression (Helicos), Next generation sequencing, Single Molecule Sequencing by Synthesis (SMSS) (Helicos), massively-parallel sequencing, Clonal Single Molecule Array (Solexa), shotgun sequencing, Ion Torrent, Oxford Nanopore, Roche Genia, Maxim-Gilbert sequencing, primer walking, sequencing using PacBio, SOLiD, Ion Torrent, or Nanopore platforms. Sequencing reactions can be performed in a variety of sample processing units, which may be multiple lanes, multiple channels, multiple wells, or other means of processing multiple sample sets substantially simultaneously. Sample processing unit can also include multiple sample chambers to enable processing of multiple runs simultaneously.

The sequencing reactions can be performed on one or more fragments types known to contain markers of cancer of other disease. The sequencing reactions can also be performed on any nucleic acid fragments present in the sample. The sequence reactions may provide for sequence coverage of the genome of at least 5%, 10%, 15%, 20%, 25%, 30%, 40%, 50%, 60%, 70%, 80%, 90%, 95%, 99%, 99.9%, or 100%. In other cases, sequence coverage of the genome may be less than 5%, 10%, 15%, 20%, 25%, 30%, 40%, 50%, 60%, 70%, 80%, 90%, 95%, 99%, 99.9%, or 100%.

Simultaneous sequencing reactions may be performed using multiplex sequencing. In some cases, cell free polynucleotides may be sequenced with at least 1000, 2000, 3000, 4000, 5000, 6000, 7000, 8000, 9000, 10000, 50000, or 100,000 sequencing reactions. In other cases, cell free polynucleotides may be sequenced with less than 1000, 2000, 3000, 4000, 5000, 6000, 7000, 8000, 9000, 10000, 50000, or 100,000 sequencing reactions. Sequencing reactions may be performed sequentially or simultaneously. Subsequent data analysis may be performed on all or part of the sequencing reactions. In some cases, data analysis may be performed on at least 1000, 2000, 3000, 4000, 5000, 6000, 7000, 8000, 9000, 10000, 50000, or 100,000 sequencing reactions. In other cases, data analysis may be performed on less than 1000, 2000, 3000, 4000, 5000, 6000, 7000, 8000, 9000, 10000, 50000, or 100,000 sequencing reactions. An exemplary read depth is 1000-50000 reads per locus (base).

F. Analysis

Sequencing according to embodiments of the disclosure generates a plurality of sequence reads. Sequence reads according to the disclosure generally include sequences of nucleotide data less than about 150 bases in length, or less than about 90 bases in length. In certain embodiments, reads are between about 80 and about 90 bases, e.g., about 85 bases in length. In some embodiments, methods of the disclosure are applied to very short reads, i.e., less than about 50 or about 30 bases in length. Sequence read data can include the sequence data as well as meta information. Sequence read data can be stored in any suitable file format including, for example, VCF files, FASTA files or FASTQ files, as are known to those of skill in the art.

FASTA is originally a computer program for searching sequence databases and the name FASTA has come to also refer to a standard file format. See Pearson & Lipman, 1988, Improved tools for biological sequence comparison, PNAS 85:2444-2448. A sequence in FASTA format begins with a single-line description, followed by lines of sequence data. The description line is distinguished from the sequence data by a greater-than (">") symbol in the first column. The word following the ">" symbol is the identifier of the sequence, and the rest of the line is the description (both are optional). There should be no space between the ">" and the first letter of the identifier. It is recommended that all lines of text be shorter than 80 characters. The sequence ends if another line starting with a ">" appears; this indicates the start of another sequence.

The FASTQ format is a text-based format for storing both a biological sequence (usually nucleotide sequence) and its corresponding quality scores. It is similar to the FASTA format but with quality scores following the sequence data. Both the sequence letter and quality score are encoded with a single ASCII character for brevity. The FASTQ format is a de facto standard for storing the output of high throughput sequencing instruments such as the Illumina Genome Analyzer. Cock et al., 2009, The Sanger FASTQ file format for sequences with quality scores, and the Solexa/Illumina FASTQ variants, Nucleic Acids Res 38(6):1767-1771.

For FASTA and FASTQ files, meta information includes the description line and not the lines of sequence data. In some embodiments, for FASTQ files, the meta information includes the quality scores. For FASTA and FASTQ files, the sequence data begins after the description line and is present typically using some subset of IUPAC ambiguity codes optionally with "-". In a preferred embodiment, the sequence data will use the A, T, C, G, and N characters, optionally including "-" or U as-needed (e.g., to represent gaps or uracil).

In some embodiments, the at least one master sequence read file and the output file are stored as plain text files (e.g., using encoding such as ASCII; ISO/IEC 646; EBCDIC; UTF-8; or UTF-16). A computer system provided by the invention may include a text editor program capable of opening the plain text files. A text editor program may refer to a computer program capable of presenting contents of a text file (such as a plain text file) on a computer screen, allowing a human to edit the text (e.g., using a monitor, keyboard, and mouse). Exemplary text editors include, without limit, Microsoft Word, emacs, pico, vi, BBEdit, and TextWrangler. Preferably, the text editor program is capable of displaying the plain text files on a computer screen, showing the meta information and the sequence reads in a human-readable format (e.g., not binary encoded but instead using alphanumeric characters as they would be used in print human writing).

While methods have been discussed with reference to FASTA or FASTQ files, methods and systems of the disclosure may be used to compress any suitable sequence file format including, for example, files in the Variant Call Format (VCF) format. A typical VCF file will include a header section and a data section. The header contains an arbitrary number of meta-information lines, each starting with characters '##', and a TAB delimited field definition line starting with a single '#' character. The field definition line names eight mandatory columns and the body section contains lines of data populating the columns defined by the field definition line. The VCF format is described in Danecek et al., 2011, The variant call format and VCFtools, Bioinformatics 27(15):2156-2158. The header section may be treated as the meta information to write to the compressed files and the data section may be treated as the lines, each of which will be stored in a master file only if unique.

Certain embodiments of the disclosure provide for the assembly of sequence reads. In assembly by alignment, for example, the reads are aligned to each other or to a reference. By aligning each read, in turn to a reference genome, all of the reads are positioned in relationship to each other to create the assembly. In addition, aligning or mapping the sequence read to a reference sequence can also be used to identify variant sequences within the sequence read. Identifying variant sequences can be used in combination with the methods and systems described herein to further aid in the diagnosis or prognosis of a disease or condition, or for guiding treatment decisions.

In some embodiments, any or all of the steps are automated. Alternatively, methods of the invention may be embodied wholly or partially in one or more dedicated programs, for example, each optionally written in a compiled language such as C++ then compiled and distributed as a binary. Methods of the invention may be implemented wholly or in part as modules within, or by invoking functionality within, existing sequence analysis platforms. In certain embodiments, methods of the invention include a number of steps that are all invoked automatically responsive to a single starting queue (e.g., one or a combination of triggering events sourced from human activity, another computer program, or a machine). Thus, the invention provides methods in which any or the steps or any combination of the steps can occur automatically responsive to a queue. Automatically generally means without intervening human input, influence, or interaction (i.e., responsive only to original or pre-queue human activity).

The system also encompasses various forms of output, which includes an accurate and sensitive interpretation of the subject nucleic acid. The output of retrieval can be provided in the format of a computer file. In certain embodiments, the output is a FASTA file, FASTQ file, or VCF file. Output may be processed to produce a text file, or an XML file containing sequence data such as a sequence of the nucleic acid aligned to a sequence of the reference genome. In other embodiments, processing yields output containing coordinates or a string describing one or more mutations in the subject nucleic acid relative to the reference genome. Alignment strings known in the art include Simple UnGapped Alignment Report (SUGAR), Verbose Useful Labeled Gapped Alignment Report (VULGAR), and Compact Idiosyncratic Gapped Alignment Report (CIGAR) (Ning, Z., et al., Genome Research 11(10):1725-9 (2001)). These strings are implemented, for example, in the Exonerate sequence alignment software from the European Bioinformatics Institute (Hinxton, UK).

In some embodiments, a sequence alignment is produced—such as, for example, a sequence alignment map (SAM) or binary alignment map (BAM) file—comprising a CIGAR string (the SAM format is described, e.g., in Li, et al., The Sequence Alignment/Map format and SAMtools, Bioinformatics, 2009, 25(16):2078-9). In some embodiments, CIGAR displays or includes gapped alignments one-per-line. CIGAR is a compressed pairwise alignment format reported as a CIGAR string. A CIGAR string is useful for representing long (e.g. genomic) pairwise alignments. A CIGAR string is used in SAM format to represent alignments of reads to a reference genome sequence.

A CIGAR string follows an established motif. Each character is preceded by a number, giving the base counts of the event. Characters used can include M, I, D, N, and S (M=match; 1=insertion; D=deletion; N=gap; S=substitution). The CIGAR string defines the sequence of matches/mismatches and deletions (or gaps). For example, the CIGAR string 2MD3M2D2M will mean that the alignment contains 2 matches, 1 deletion (number 1 is omitted in order to save some space), 3 matches, 2 deletions and 2 matches.

As contemplated by the invention, the functions described above can be implemented using a system that includes software, hardware, firmware, hardwiring, or any combinations of these. Features implementing functions can also be physically located at various positions, including being distributed such that portions of functions are implemented at different physical locations.

As system may include one or more of a server computer, a terminal, a sequencer, a sequencer computer, a computer, or any combination thereof. Each such computer device may communicate via network. Sequencer may optionally include or be operably coupled to its own, e.g., dedicated, sequencer computer (including any input/output mechanisms (I/O), processor, and memory). Additionally or alternatively, sequencer may be operably coupled to a server or computer (e.g., laptop, desktop, or tablet) via network. Computer includes one or more processor, memory, and I/O. Where methods of the invention employ a client/server architecture, any steps of methods of the invention may be performed using server, which includes one or more of processor, memory, and I/O, capable of obtaining data, instructions, etc., or providing results via an interface module or providing results as a file. Server may be engaged over network through computer or terminal, or server may be directly connected to terminal. Terminal is preferably a computer device. A computer according to the invention preferably includes one or more processor coupled to an I/O mechanism and memory.

A processor may be provided by one or more processors including, for example, one or more of a single core or multi-core processor. An I/O mechanism may include a video display unit (e.g., a liquid crystal display (LCD) or a cathode ray tube (CRT)), an alphanumeric input device (e.g., a keyboard), a cursor control device (e.g., a mouse), a disk drive unit, a signal generation device (e.g., a speaker), an accelerometer, a microphone, a cellular radio frequency antenna, and a network interface device (e.g., a network interface card (NIC), Wi-Fi card, cellular modem, data jack, Ethernet port, modem jack, HDMI port, mini-HDMI port, USB port), touchscreen (e.g., CRT, LCD, LED, AMOLED, Super AMOLED), pointing device, trackpad, light (e.g., LED), light/image projection device, or a combination thereof. Memory according to the invention refers to a non-transitory memory which is provided by one or more tangible devices which preferably include one or more machine-readable medium on which is stored one or more sets of instructions (e.g., software) embodying any one or more of the methodologies or functions described herein. The software may also reside, completely or at least partially, within the main memory, processor, or both during execution thereof by a computer within system, the main memory and the processor also constituting machine-readable media. The software may further be transmitted or received over a network via the network interface device.

While the machine-readable medium can in an exemplary embodiment be a single medium, the term "machine-readable medium" should be taken to include a single medium or multiple media (e.g., a centralized or distributed database, and/or associated caches and servers) that store the one or more sets of instructions. The term "machine-readable medium" shall also be taken to include any medium that is capable of storing, encoding or carrying a set of instructions for execution by the machine and that cause the machine to perform any one or more of the methodologies of the present invention. Memory may be, for example, one or more of a hard disk drive, solid state drive (SSD), an optical disc, flash memory, zip disk, tape drive, "cloud" storage location, or a combination thereof. In certain embodiments, a device of the invention includes a tangible, non-transitory computer readable medium for memory. Exemplary devices for use as memory include semiconductor memory devices, (e.g., EPROM, EEPROM, solid state drive (SSD), and flash memory devices e.g., SD, micro SD, SDXC, SDIO, SDHC cards); magnetic disks, (e.g., internal hard disks or removable disks); and optical disks (e.g., CD and DVD disks).

In some embodiments, the results of the systems and methods disclosed herein are used as an input to generate a report. The report may be in a paper format. For example, a report may include data derived from the filtered sequence information, as identified by the methods and systems disclosed herein. Such data may include, for example, diagnostic information or therapeutic recommendations in view of the identified sequence information. In some embodiments the report may include information, such as one or more true genetic variants, as identified by the methods and systems disclosed herein.

The various steps of the methods disclosed herein, or the steps carried out by the systems disclosed herein, may be carried out at the same or different times, in the same or different geographical locations, e.g., countries, and/or by the same or different people.

III. Exemplary Applications

A. Sequencing Panel

To improve the likelihood of detecting tumor indicating mutations, the region of DNA sequenced may comprise a panel of genes or genomic regions. Selection of a limited region for sequencing (e.g., a limited panel) can reduce the total sequencing needed (e.g., a total amount of nucleotides sequenced. A sequencing panel can target a plurality of different genes or regions to detect a single cancer, a set of cancers, or all cancers. Alternatively, DNA may be sequenced by whole genome sequencing (WGS) or other unbiased sequencing method without the use of a sequencing panel.

In some aspects, a panel that targets a plurality of different genes or genomic regions is selected such that a determined proportion of subjects having a cancer exhibits a genetic variant or tumor marker in one or more different genes in the panel. The panel may be selected to limit a region for sequencing to a fixed number of base pairs. The panel may be selected to sequence a desired amount of DNA. The panel may be further selected to achieve a desired sequence read depth. The panel may be selected to achieve a desired sequence read depth or sequence read coverage for an amount of sequenced base pairs. The panel may be selected to achieve a theoretical sensitivity, a theoretical specificity, and/or a theoretical accuracy for detecting one or more genetic variants in a sample.

Probes for detecting the panel of regions can include those for detecting genomic regions of interest (hotspot regions) as well as nucleosome-aware probes (e.g., KRAS codons 12 and 13) and may be designed to optimize capture based on analysis of cfDNA coverage and fragment size variation impacted by nucleosome binding patterns and GC sequence composition. Regions used herein can also include non-hotspot regions optimized based on nucleosome positions and GC models. The panel can comprise a plurality of subpanels, including subpanels for identifying tissue of origin (e.g., use of published literature to define 50-100 baits representing genes with most diverse transcription profile across tissues (not necessarily promoters)), whole genome scaffold (e.g., for identifying ultra-conservative genomic content and tiling sparsely across chromosomes with handful of probes for copy number base lining purposes), transcription start site (TSS)/CpG islands (e.g., for capturing differential methylated regions (e.g., Differentially Methylated Regions (DMRs)) in for example in promoters of tumor suppressor genes (e.g., SEPT9/VIM in colorectal cancer)). In some embodiments, markers for a tissue of origin are tissue-specific epigenetic markers.

Some examples of listings of genomic locations of interest may be found in Table 1 and Table 2. In some embodiments, genomic locations used in the methods of the present disclosure comprise at least a portion of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, or 97 of the genes of Table 1. In some embodiments, genomic locations used in the methods of the present disclosure comprise at least 5, at least 10, at least 15, at least 20, at least 25, at least 30, at least 35, at least 40, at least 45, at least 50, at least 55, at least 60, at least 65, or 70 of the SNVs of Table 1. In some embodiments, genomic locations used in the methods of the present disclosure comprise at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the CNVs of Table 1. In some embodiments, genomic locations used in the methods of the present disclosure comprise at least 1, at least 2, at least 3, at least 4, at least 5, or 6 of the fusions of Table 1. In some embodiments, genomic locations used in the methods of the present disclosure comprise at least a portion of at least 1, at least 2, or 3 of the indels of Table 1. In some embodiments, genomic locations used in the methods of the present disclosure comprise at least a portion of at least 5, at least 10, at least 15, at least 20, at least 25, at least 30, at least 35, at least 40, at least 45, at least 50, at least 55, at least 60, at least 65, at least 70, at least 75, at least 80, at least 85, at least 90, at least 95, at least 100, at least 105, at least 110, or 115 of the genes of Table 2. In some embodiments, genomic locations used in the methods of the present disclosure comprise at least 5, at least 10, at least 15, at least 20, at least 25, at least 30, at least 35, at least 40, at least 45, at least 50, at least 55, at least 60, at least 65, at least 70, or 73 of the SNVs of Table 2. In some embodiments, genomic locations used in the methods of the present disclosure comprise at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the CNVs of Table 2. In some embodiments, genomic locations used in the methods of the present disclosure comprise at least 1, at least 2, at least 3, at least 4, at least 5, or 6 of the fusions of Table 2. In some embodiments, genomic locations used in the methods of the present disclosure comprise at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, or 18 of the indels of Table 2. Each of these genomic locations of interest may be identified as a backbone region or hot-spot region for a given bait set panel. An example of a listing of hot-spot genomic locations of interest may be found in Table 3. In some embodiments, genomic locations used in the methods of the present disclosure comprise at least a portion of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 of the genes of Table 3. Each hot-spot genomic location is listed with several characteristics, including the associated gene, chromosome on which it resides, the start and stop position of the genome representing the gene's locus, the length of the gene's locus in base pairs, the exons covered by the gene, and the critical feature (e.g., type of mutation) that a given genomic location of interest may seek to capture.

TABLE 1

| Point Mutations (SNVs) | | | | | | Amplifications (CNVs) | | Fusions | Indels |
| --- | --- | --- | --- | --- | --- | --- | --- | --- | --- |
| AKT1 | ALK | APC | AR | ARAF | ARID1A | AR | BRAF | ALK | EGFR |
| ATM | BRAF | BRCA1 | BRCA2 | CCND1 | CCND2 | CCND1 | CCND2 | FGFR2 | (exons |
| CCNE1 | CDH1 | CDK4 | CDK6 | CDKN2A | CDKN2B | CCNE1 | CDK4 | FGFR3 | 19 & 20) |
| CTNNB1 | EGFR | ERBB2 | ESR1 | EZH2 | FBXW7 | CDK6 | EGFR | NTRK1 | ERBB2 |
| FGFR1 | FGFR2 | FGFR3 | GATA3 | GNA11 | GNAQ | ERBB2 | FGFR1 | RET | (exons |
| GNAS | HNF1A | HRAS | IDH1 | IDH2 | JAK2 | FGFR2 | KIT | ROS1 | 19 & 20) |
| JAK3 | KIT | KRAS | MAP2K1 | MAP2K2 | MET | KRAS | MET | | MET |
| MLH1 | MPL | MYC | NF1 | NFE2L2 | NOTCH1 | MYC | PDGFRA | | (exon 14 |
| NPM1 | NRAS | NTRK1 | PDGFRA | PIK3CA | PTEN | PIK3CA | RAF1 | | skipping) |
| PTPN11 | RAF1 | RB1 | RET | RHEB | RHOA | | | | |
| RIT1 | ROS1 | SMAD4 | SMO | SRC | STK11 | | | | |
| TERT | TP53 | TSC1 | VHL | | | | | | |

TABLE 2

| Point Mutations (SNVs) | | | | | | Amplifications (CNVs) | | Fusions | Indels |
|---|---|---|---|---|---|---|---|---|---|
| AKT1 | ALK | APC | AR | ARAF | ARID1A | AR | BRAF | ALK | EGFR |
| ATM | BRAF | BRCA1 | BRCA2 | CCND1 | CCND2 | CCND1 | CCND2 | FGFR2 | (exons |
| CCNE1 | CDH1 | CDK4 | CDK6 | CDKN2A | DDR2 | CCNE1 | CDK4 | FGFR3 | 19 & 20) |
| CTNNB1 | EGFR | ERBB2 | ESR1 | EZH2 | FBXW7 | CDK6 | EGFR | NTRK1 | ERBB2 |
| FGFR1 | FGFR2 | FGFR3 | GATA3 | GNA11 | GNAQ | ERBB2 | FGFR1 | RET | (exons |
| GNAS | HNF1A | HRAS | IDH1 | IDH2 | JAK2 | FGFR2 | KIT | ROS1 | 19 & 20) |
| JAK3 | KIT | KRAS | MAP2K1 | MAP2K2 | MET | KRAS | MET | | MET |
| MLH1 | MPL | MYC | NF1 | NFE2L2 | NOTCH1 | MYC | PDGFRA | | (exon 14 |
| NPM1 | NRAS | NTRK1 | PDGFRA | PIK3CA | PTEN | PIK3CA | RAF1 | | skipping) |
| PTPN11 | RAF1 | RB1 | RET | RHEB | RHOA | | | | ATM |
| RIT1 | ROS1 | SMAD4 | SMO | MAPK1 | STK11 | | | | APC |
| TERT | TP53 | TSC1 | VHL | MAPK3 | MTOR | | | | ARID1A |
| NTRK3 | | | | | | | | | BRCA1 |
| | | | | | | | | | BRCA2 |
| | | | | | | | | | CDH1 |
| | | | | | | | | | CDKN2A |
| | | | | | | | | | GATA3 |
| | | | | | | | | | KIT |
| | | | | | | | | | MLH1 |
| | | | | | | | | | MTOR |
| | | | | | | | | | NF1 |
| | | | | | | | | | PDGFRA |
| | | | | | | | | | PTEN |
| | | | | | | | | | RB1 |
| | | | | | | | | | SMAD4 |
| | | | | | | | | | STK11 |
| | | | | | | | | | TP53 |
| | | | | | | | | | TSC1 |
| | | | | | | | | | VHL |

TABLE 3

| Gene | Chromosome | Start Position | Stop Position | Length (bp) | Exons Covered | Critical Feature |
|---|---|---|---|---|---|---|
| ALK | chr2 | 29446405 | 29446655 | 250 | intron 19 | Fusion |
| ALK | chr2 | 29446062 | 29446197 | 135 | intron 20 | Fusion |
| ALK | chr2 | 29446198 | 29446404 | 206 | 20 | Fusion |
| ALK | chr2 | 29447353 | 29447473 | 120 | intron 19 | Fusion |
| ALK | chr2 | 29447614 | 29448316 | 702 | intron 19 | Fusion |
| ALK | chr2 | 29448317 | 29448441 | 124 | 19 | Fusion |
| ALK | chr2 | 29449366 | 29449777 | 411 | intron 18 | Fusion |
| ALK | chr2 | 29449778 | 29449950 | 172 | 18 | Fusion |
| BRAF | chr7 | 140453064 | 140453203 | 139 | 15 | BRAF V600 |
| CTNNB1 | chr3 | 41266007 | 41266254 | 247 | 3 | S37 |
| EGFR | chr7 | 55240528 | 55240827 | 299 | 18 and 19 | G719 and deletions |
| EGFR | chr7 | 55241603 | 55241746 | 143 | 20 | Insertions/T790M |
| EGFR | chr7 | 55242404 | 55242523 | 119 | 21 | L858R |
| ERBB2 | chr17 | 37880952 | 37881174 | 222 | 20 | Insertions |
| ESR1 | chr6 | 152419857 | 152420111 | 254 | 10 | V534, P535, L536, Y537, D538 |
| FGFR2 | chr10 | 123279482 | 123279693 | 211 | 6 | S252 |
| GATA3 | chr10 | 8111426 | 8111571 | 145 | 5 | SS/Indels |
| GATA3 | chr10 | 8115692 | 8116002 | 310 | 6 | SS/Indels |
| GNAS | chr20 | 57484395 | 57484488 | 93 | 8 | R844 |
| IDH1 | chr2 | 209113083 | 209113394 | 311 | 4 | R132 |
| IDH2 | chr15 | 90631809 | 90631989 | 180 | 4 | R140, R172 |
| KIT | chr4 | 55524171 | 55524258 | 87 | 1 | |
| KIT | chr4 | 55561667 | 55561957 | 290 | 2 | |
| KIT | chr4 | 55564439 | 55564741 | 302 | 3 | |
| KIT | chr4 | 55565785 | 55565942 | 157 | 4 | |
| KIT | chr4 | 55569879 | 55570068 | 189 | 5 | |
| KIT | chr4 | 55573253 | 55573463 | 210 | 6 | |
| KIT | chr4 | 55575579 | 55575719 | 140 | 7 | |
| KIT | chr4 | 55589739 | 55589874 | 135 | 8 | |
| KIT | chr4 | 55592012 | 55592226 | 214 | 9 | |
| KIT | chr4 | 55593373 | 55593718 | 345 | 10 and 11 | 557, 559, 560, 576 |
| KIT | chr4 | 55593978 | 55594297 | 319 | 12 and 13 | V654 |
| KIT | chr4 | 55595490 | 55595661 | 171 | 14 | T670, S709 |
| KIT | chr4 | 55597483 | 55597595 | 112 | 15 | D716 |
| KIT | chr4 | 55598026 | 55598174 | 148 | 16 | L783 |

TABLE 3-continued

| Gene | Chromosome | Start Position | Stop Position | Length (bp) | Exons Covered | Critical Feature |
|---|---|---|---|---|---|---|
| KIT | chr4 | 55599225 | 55599368 | 143 | 17 | C809, R815, D816, L818, D820, 5821F, N822, Y823 |
| KIT | chr4 | 55602653 | 55602785 | 132 | 18 | A829P |
| KIT | chr4 | 55602876 | 55602996 | 120 | 19 | |
| KIT | chr4 | 55603330 | 55603456 | 126 | 20 | |
| KIT | chr4 | 55604584 | 55604733 | 149 | 21 | |
| KRAS | chr12 | 25378537 | 25378717 | 180 | 4 | A146 |
| KRAS | chr12 | 25380157 | 25380356 | 199 | 3 | Q61 |
| KRAS | chr12 | 25398197 | 25398328 | 131 | 2 | G12/G13 |
| MET | chr7 | 116411535 | 116412255 | 720 | 13, 14, intron 13, intron 14 | MET exon 14 SS |
| NRAS | chr1 | 115256410 | 115256609 | 199 | 3 | Q61 |
| NRAS | chr1 | 115258660 | 115258791 | 131 | 2 | G12/G13 |
| PIK3CA | chr3 | 178935987 | 178936132 | 145 | 10 | E545K |
| PIK3CA | chr3 | 178951871 | 178952162 | 291 | 21 | H1047R |
| PTEN | chr10 | 89692759 | 89693018 | 259 | 5 | R130 |
| SMAD4 | chr18 | 48604616 | 48604849 | 233 | 12 | D537 |
| TERT | chr5 | 1294841 | 1295512 | 671 | promoter | chr5:1295228 |
| TP53 | chr17 | 7573916 | 7574043 | 127 | 11 | Q331, R337, R342 |
| TP53 | chr17 | 7577008 | 7577165 | 157 | 8 | R273 |
| TP53 | chr17 | 7577488 | 7577618 | 130 | 7 | R248 |
| TP53 | chr17 | 7578127 | 7578299 | 172 | 6 | R213/Y220 |
| TP53 | chr17 | 7578360 | 7578564 | 204 | 5 | R175/Deletions |
| TP53 | chr17 | 7579301 | 7579600 | 299 | 4 | |
| | | | | 12574 (total target region) 16330 (total probe coverage) | | |

In some embodiments, the one or more regions in the panel comprise one or more loci from one or a plurality of genes for detecting residual cancer after surgery. This detection can be earlier than is possible for existing methods of cancer detection. In some embodiments, the one or more genomic locations in the panel comprise one or more loci from one or a plurality of genes for detecting cancer in a high-risk patient population. For example, smokers have much higher rates of lung cancer than the general population. Moreover, smokers can develop other lung conditions that make cancer detection more difficult, such as the development of irregular nodules in the lungs. In some embodiments, the methods described herein detect cancer in high risk patients earlier than is possible for existing methods of cancer detection.

A genomic location may be selected for inclusion in a sequencing panel based on a number of subjects with a cancer that have a tumor marker in that gene or region. A genomic location may be selected for inclusion in a sequencing panel based on prevalence of subjects with a cancer and a tumor marker present in that gene. Presence of a tumor marker in a region may be indicative of a subject having cancer.

In some instances, the panel may be selected using information from one or more databases. The information regarding a cancer may be derived from cancer tumor biopsies or cfDNA assays. A database may comprise information describing a population of sequenced tumor samples. A database may comprise information about mRNA expression in tumor samples. A databased may comprise information about regulatory elements or genomic regions in tumor samples. The information relating to the sequenced tumor samples may include the frequency various genetic variants and describe the genes or regions in which the genetic variants occur. The genetic variants may be tumor markers. A non-limiting example of such a database is COSMIC. COSMIC is a catalogue of somatic mutations found in various cancers. For a particular cancer, COSMIC ranks genes based on frequency of mutation. A gene may be selected for inclusion in a panel by having a high frequency of mutation within a given gene. For instance, COSMIC indicates that 33% of a population of sequenced breast cancer samples have a mutation in TP53 and 22% of a population of sampled breast cancers have a mutation in KRAS. Other ranked genes, including APC, have mutations found only in about 4% of a population of sequenced breast cancer samples. TP53 and KRAS may be included in a sequencing panel based on having relatively high frequency among sampled breast cancers (compared to APC, for example, which occurs at a frequency of about 4%). COSMIC is provided as a non-limiting example, however, any database or set of information may be used that associates a cancer with tumor marker located in a gene or genetic region. In another example, as provided by COSMIC, of 1156 biliary tract cancer samples, 380 samples (33%) carried mutations in TP53. Several other genes, such as APC, have mutations in 4-8% of all samples. Thus, TP53 may be selected for inclusion in the panel based on a relatively high frequency in a population of biliary tract cancer samples.

A gene or genomic section may be selected for a panel where the frequency of a tumor marker is significantly greater in sampled tumor tissue or circulating tumor DNA than found in a given background population. A combination of genomic locations may be selected for inclusion of a panel such that at least a majority of subjects having a cancer may have a tumor marker or genomic region present in at least one of the genomic location or genes in the panel. The combination of genomic location may be selected based on data indicating that, for a particular cancer or set of cancers, a majority of subjects have one or more tumor markers in one or more of the selected regions. For example, to detect cancer 1, a panel comprising regions A, B, C, and/or D may be selected based on data indicating that 90% of subjects with cancer 1 have a tumor marker in regions A, B, C, and/or D of the panel. Alternately, tumor markers may be shown to occur independently in two or more regions in subjects having a cancer such that, combined, a tumor marker in the two or more regions is present in a majority of a population of subjects having a cancer. For example, to detect cancer 2, a panel comprising regions X, Y, and Z may be selected based on data indicating that 90% of subjects have a tumor marker in one or more regions, and in 30% of such subjects a tumor marker is detected only in region X, while tumor markers are detected only in regions Y and/or Z for the remainder of the subjects for whom a tumor marker was detected. Tumor markers present in one or more genomic locations previously shown to be associated with one or more cancers may be indicative of or predictive of a subject having cancer if a tumor marker is detected in one or more of those regions 50% or more of the time. Computational approaches such as models employing conditional probabilities of detecting cancer given a cancer frequency for a set of tumor markers within one or more regions may be used to predict which regions, alone or in combination, may be predictive of cancer. Other approaches for panel selection involve the use of databases describing information from studies employing comprehensive genomic profiling of tumors with large panels and/or whole genome sequencing (WGS, RNA-seq, Chip-seq, bisulfate sequencing, ATAC-seq, and others). Information gleaned from literature may also describe pathways commonly affected and mutated in certain cancers. Panel selection may be further informed by the use of ontologies describing genetic information.

Genes included in the panel for sequencing can include the fully transcribed region, the promoter region, enhancer regions, regulatory elements, and/or downstream sequence. To further increase the likelihood of detecting tumor indicating mutations only exons may be included in the panel. The panel can comprise all exons of a selected gene, or only one or more of the exons of a selected gene. The panel may comprise of exons from each of a plurality of different genes. The panel may comprise at least one exon from each of the plurality of different genes.

In some aspects, a panel of exons from each of a plurality of different genes is selected such that a determined proportion of subjects having a cancer exhibit a genetic variant in at least one exon in the panel of exons.

At least one full exon from each different gene in a panel of genes may be sequenced. The sequenced panel may comprise exons from a plurality of genes. The panel may comprise exons from 2 to 100 different genes, from 2 to 70 genes, from 2 to 50 genes, from 2 to 30 genes, from 2 to 15 genes, or from 2 to 10 genes.

A selected panel may comprise a varying number of exons. The panel may comprise from 2 to 3000 exons. The panel may comprise from 2 to 1000 exons. The panel may comprise from 2 to 500 exons. The panel may comprise from 2 to 100 exons. The panel may comprise from 2 to 50 exons. The panel may comprise no more than 300 exons. The panel may comprise no more than 200 exons. The panel may comprise no more than 100 exons. The panel may comprise no more than 50 exons. The panel may comprise no more than 40 exons. The panel may comprise no more than 30 exons. The panel may comprise no more than 25 exons. The panel may comprise no more than 20 exons. The panel may comprise no more than 15 exons. The panel may comprise no more than 10 exons. The panel may comprise no more than 9 exons. The panel may comprise no more than 8 exons. The panel may comprise no more than 7 exons.

The panel may comprise one or more exons from a plurality of different genes. The panel may comprise one or more exons from each of a proportion of the plurality of different genes. The panel may comprise at least two exons from each of at least 25%, 50%, 75% or 90% of the different genes. The panel may comprise at least three exons from each of at least 25%, 50%, 75% or 90% of the different genes. The panel may comprise at least four exons from each of at least 25%, 50%, 75% or 90% of the different genes.

The sizes of the sequencing panel may vary. A sequencing panel may be made larger or smaller (in terms of nucleotide size) depending on several factors including, for example, the total amount of nucleotides sequenced or a number of unique molecules sequenced for a particular region in the panel. The sequencing panel can be sized 5 kb to 50 kb. The sequencing panel can be 10 kb to 30 kb in size. The sequencing panel can be 12 kb to 20 kb in size. The sequencing panel can be 12 kb to 60 kb in size. The sequencing panel can be at least 10 kb, 12 kb, 15 kb, 20 kb, 25 kb, 30 kb, 35 kb, 40 kb, 45 kb, 50 kb, 60 kb, 70 kb, 80 kb, 90 kb, 100 kb, 110 kb, 120 kb, 130 kb, 140 kb, or 150 kb in size. The sequencing panel may be less than 100 kb, 90 kb, 80 kb, 70 kb, 60 kb, or 50 kb in size.

The panel selected for sequencing can comprise at least 1, 5, 10, 15, 20, 25, 30, 40, 50, 60, 80, or 100 genomic locations (e.g., that each include genomic regions of interest). In some cases, the genomic locations in the panel are selected that the size of the locations are relatively small. In some cases, the regions in the panel have a size of about 10 kb or less, about 8 kb or less, about 6 kb or less, about 5 kb or less, about 4 kb or less, about 3 kb or less, about 2.5 kb or less, about 2 kb or less, about 1.5 kb or less, or about 1 kb or less or less. In some cases, the genomic locations in the panel have a size from about 0.5 kb to about 10 kb, from about 0.5 kb to about 6 kb, from about 1 kb to about 11 kb, from about 1 kb to about 15 kb, from about 1 kb to about 20 kb, from about 0.1 kb to about 10 kb, or from about 0.2 kb to about 1 kb. For example, the regions in the panel can have a size from about 0.1 kb to about 5 kb.

The panel selected herein can allow for deep sequencing that is sufficient to detect low-frequency genetic variants (e.g., in cell-free nucleic acid molecules obtained from a sample). An amount of genetic variants in a sample may be referred to in terms of the minor allele frequency for a given genetic variant. The minor allele frequency may refer to the frequency at which minor alleles (e.g., not the most common allele) occurs in a given population of nucleic acids, such as a sample. Genetic variants at a low minor allele frequency may have a relatively low frequency of presence in a sample. In some cases, the panel allows for detection of genetic variants at a minor allele frequency of at least 0.0001%, 0.001%, 0.005%, 0.01%, 0.05%, 0.1%, or 0.5%. The panel can allow for detection of genetic variants at a minor allele frequency of 0.001% or greater. The panel can allow for detection of genetic variants at a minor allele frequency of 0.01% or greater. The panel can allow for detection of genetic variant present in a sample at a frequency of as low as 0.0001%, 0.001%, 0.005%, 0.01%, 0.025%, 0.05%, 0.075%, 0.1%, 0.25%, 0.5%, 0.75%, or 1.0%. The panel can allow for detection of tumor markers present in a sample at a frequency of at least 0.0001%, 0.001%, 0.005%, 0.01%, 0.025%, 0.05%, 0.075%, 0.1%, 0.25%, 0.5%, 0.75%, or 1.0%. The panel can allow for detection of tumor markers at a frequency in a sample as low as 1.0%. The panel can allow for detection of tumor markers at a frequency in a sample as low as 0.75%. The panel can allow for detection of tumor markers at a frequency in a sample as low as 0.5%. The panel can allow for detection of tumor markers at a frequency in a sample as low as 0.25%. The panel can allow for detection of tumor markers at a frequency in a sample as low as 0.1%. The panel can allow for detection of tumor markers at a frequency in a sample as low as 0.075%. The panel can allow for detection of tumor markers at a frequency in a sample as low as 0.05%. The panel can allow for detection of tumor markers at a frequency in a sample as low as 0.025%. The panel can allow for detection of tumor markers at a frequency in a sample as low as 0.01%. The panel can allow for detection of tumor markers at a frequency in a sample as low as 0.005%. The panel can allow for detection of tumor markers at a frequency in a sample as low as 0.001%. The panel can allow for detection of tumor markers at a frequency in a sample as low as 0.0001%. The panel can allow for detection of tumor markers in sequenced cfDNA at a frequency in a sample as low as 1.0% to 0.0001%. The panel can allow for detection of tumor markers in sequenced cfDNA at a frequency in a sample as low as 0.01% to 0.0001%.

A genetic variant can be exhibited in a percentage of a population of subjects who have a disease (e.g., cancer). In some cases, at least 1%, 2%, 3%, 5%, 10%, 20%, 30%, 40%, 50%, 60%, 70%, 80%, 90%, 95%, or 99% of a population having the cancer exhibit one or more genetic variants in at least one of the regions in the panel. For example, at least 80% of a population having the cancer may exhibit one or more genetic variants in at least one of the genomic positions in the panel.

The panel can comprise one or more locations comprising genomic regions of interest from each of one or more genes. In some cases, the panel can comprise one or more locations comprising genomic regions of interest from each of at least 1, 2, 3, 4, 5, 6, 7, 8, 9, 10, 15, 20, 25, 30, 40, 50, or 80 genes. In some cases, the panel can comprise one or more locations comprising genomic regions of interest from each of at most 1, 2, 3, 4, 5, 6, 7, 8, 9, 10, 15, 20, 25, 30, 40, 50, or 80 genes. In some cases, the panel can comprise one or more locations comprising genomic regions of interest from each of from about 1 to about 80, from 1 to about 50, from about 3 to about 40, from 5 to about 30, from 10 to about 20 different genes.

The regions in the panel can be selected so that they comprise sequences differentially transcribed across one or more tissues. In some cases, the locations comprising genomic regions can comprise sequences transcribed in certain tissues at a higher level compared to other tissues. For example, the locations comprising genomic regions can comprise sequences transcribed in certain tissues but not in other tissues.

The genomic locations in the panel can comprise coding and/or non-coding sequences. For example, the genomic locations in the panel can comprise one or more sequences in exons, introns, promoters, 3' untranslated regions, 5' untranslated regions, regulatory elements, transcription start sites, and/or splice sites. In some cases, the regions in the panel can comprise other non-coding sequences, including pseudogenes, repeat sequences, transposons, viral elements, and telomeres. In some cases, the genomic locations in the panel can comprise sequences in non-coding RNA, e.g., ribosomal RNA, transfer RNA, Piwi-interacting RNA, and microRNA.

The genomic locations in the panel can be selected to detect (diagnose) a cancer with a desired level of sensitivity (e.g., through the detection of one or more genetic variants). For example, the regions in the panel can be selected to detect the cancer (e.g., through the detection of one or more genetic variants) with a sensitivity of at least 50%, 55%, 60%, 65%, 70%, 75%, 80%, 85%, 90%, 95%, 96%, 97%, 98%, 99%, 99.5%, or 99.9%. The genomic locations in the panel can be selected to detect the cancer with a sensitivity of 100%.

The genomic locations in the panel can be selected to detect (diagnose) a cancer with a desired level of specificity (e.g., through the detection of one or more genetic variants). For example, the genomic locations in the panel can be selected to detect cancer (e.g., through the detection of one or more genetic variants) with a specificity of at least 50%, 55%, 60%, 65%, 70%, 75%, 80%, 85%, 90%, 95%, 96%, 97%, 98%, 99%, 99.5%, or 99.9%. The genomic locations in the panel can be selected to detect the one or more genetic variant with a specificity of 100%.

The genomic locations in the panel can be selected to detect (diagnose) a cancer with a desired positive predictive value. Positive predictive value can be increased by increasing sensitivity (e.g., chance of an actual positive being detected) and/or specificity (e.g., chance of not mistaking an actual negative for a positive). As a non-limiting example, genomic locations in the panel can be selected to detect the one or more genetic variant with a positive predictive value of at least 50%, 55%, 60%, 65%, 70%, 75%, 80%, 85%, 90%, 95%, 96%, 97%, 98%, 99%, 99.5%, or 99.9%. The regions in the panel can be selected to detect the one or more genetic variant with a positive predictive value of 100%.

The genomic locations in the panel can be selected to detect (diagnose) a cancer with a desired accuracy. As used herein, the term "accuracy" may refer to the ability of a test to discriminate between a disease condition (e.g., cancer) and healthy condition. Accuracy may be can be quantified using measures such as sensitivity and specificity, predictive values, likelihood ratios, the area under the ROC curve, Youden's index and/or diagnostic odds ratio.

Accuracy may presented as a percentage, which refers to a ratio between the number of tests giving a correct result and the total number of tests performed. The regions in the panel can be selected to detect cancer with an accuracy of at least 50%, 55%, 60%, 65%, 70%, 75%, 80%, 85%, 90%, 95%, 96%, 97%, 98%, 99%, 99.5%, or 99.9%. The genomic locations in the panel can be selected to detect cancer with an accuracy of 100%.

A panel may be selected to be highly sensitive and detect low frequency genetic variants. For instance, a panel may be selected such that a genetic variant or tumor marker present in a sample at a frequency as low as 0.01%, 0.05%, or 0.001% may be detected at a sensitivity of at least 50%, 55%, 60%, 65%, 70%, 75%, 80%, 85%, 90%, 95%, 96%, 97%, 98%, 99%, 99.5%, or 99.9%. Genomic locations in a panel may be selected to detect a tumor marker present at a frequency of 1% or less in a sample with a sensitivity of 70% or greater. A panel may be selected to detect a tumor marker at a frequency in a sample as low as 0.1% with a sensitivity of at least 50%, 55%, 60%, 65%, 70%, 75%, 80%, 85%, 90%, 95%, 96%, 97%, 98%, 99%, 99.5%, or 99.9%. A panel may be selected to detect a tumor marker at a frequency in a sample as low as 0.01% with a sensitivity of at least 50%, 55%, 60%, 65%, 70%, 75%, 80%, 85%, 90%, 95%, 96%, 97%, 98%, 99%, 99.5%, or 99.9%. A panel may be selected to detect a tumor marker at a frequency in a sample as low as 0.001% with a sensitivity of at least 50%, 55%, 60%, 65%, 70%, 75%, 80%, 85%, 90%, 95%, 96%, 97%, 98%, 99%, 99.5%, or 99.9%.

A panel may be selected to be highly specific and detect low frequency genetic variants. For instance, a panel may be selected such that a genetic variant or tumor marker present in a sample at a frequency as low as 0.01%, 0.05%, or 0.001% may be detected at a specificity of at least 50%, 55%, 60%, 65%, 70%, 75%, 80%, 85%, 90%, 95%, 96%, 97%, 98%, 99%, 99.5%, or 99.9%. Genomic locations in a panel may be selected to detect a tumor marker present at a frequency of 1% or less in a sample with a specificity of 70% or greater. A panel may be selected to detect a tumor marker at a frequency in a sample as low as 0.1% with a specificity of at least 70%, 75%, 80%, 85%, 90%, 95%, 96%, 97%, 98%, 99%, 99.5%, or 99.9%. A panel may be selected to detect a tumor marker at a frequency in a sample as low as 0.01% with a specificity of at least 70%, 75%, 80%, 85%, 90%, 95%, 96%, 97%, 98%, 99%, 99.5%, or 99.9%. A panel may be selected to detect a tumor marker at a frequency in a sample as low as 0.001% with a specificity of at least 70%, 75%, 80%, 85%, 90%, 95%, 96%, 97%, 98%, 99%, 99.5%, or 99.9%.

A panel may be selected to be highly accurate and detect low frequency genetic variants. A panel may be selected such that a genetic variant or tumor marker present in a sample at a frequency as low as 0.01%, 0.05%, or 0.001% may be detected at an accuracy of at least 70%, 75%, 80%, 85%, 90%, 95%, 96%, 97%, 98%, 99%, 99.5%, or 99.9%. Genomic locations in a panel may be selected to detect a tumor marker present at a frequency of 1% or less in a sample with an accuracy of 70% or greater. A panel may be selected to detect a tumor marker at a frequency in a sample as low as 0.1% with an accuracy of at least 70%, 75%, 80%, 85%, 90%, 95%, 96%, 97%, 98%, 99%, 99.5%, or 99.9%. A panel may be selected to detect a tumor marker at a frequency in a sample as low as 0.01% with an accuracy of at least 70%, 75%, 80%, 85%, 90%, 95%, 96%, 97%, 98%, 99%, 99.5%, or 99.9%. A panel may be selected to detect a tumor marker at a frequency in a sample as low as 0.001% with an accuracy of at least 70%, 75%, 80%, 85%, 90%, 95%, 96%, 97%, 98%, 99%, 99.5%, or 99.9%.

A panel may be selected to be highly predictive and detect low frequency genetic variants. A panel may be selected such that a genetic variant or tumor marker present in a sample at a frequency as low as 0.01%, 0.05%, or 0.001% may have a positive predictive value of at least 70%, 75%, 80%, 85%, 90%, 95%, 96%, 97%, 98%, 99%, 99.5%, or 99.9%.

The concentration of probes or baits used in the panel may be increased (2 to 6 ng/µL) to capture more nucleic acid molecule within a sample. The concentration of probes or baits used in the panel may be at least 2 ng/µL, 3 ng/µL, 4 ng/µL, 5 ng/µL, 6 ng/µL, or greater. The concentration of probes may be about 2 ng/µL to about 3 ng/µL, about 2 ng/µL to about 4 ng/µL, about 2 ng/µL to about 5 ng/µL, about 2 ng/µL to about 6 ng/µL. The concentration of probes or baits used in the panel may be 2 ng/µL or more to 6 ng/µL or less. In some instances this may allow for more molecules within a biological to be analyzed thereby enabling lower frequency alleles to be detected.

B. Cancer and Other Diseases

In certain embodiments, the methods and aspects disclosed herein are used to diagnose a given disease, disorder or condition in patients. Typically, the disease under consideration is a type of cancer. Non-limiting examples of such cancers include biliary tract cancer, bladder cancer, transitional cell carcinoma, urothelial carcinoma, brain cancer, gliomas, astrocytomas, breast carcinoma, metaplastic carcinoma, cervical cancer, cervical squamous cell carcinoma, rectal cancer, colorectal carcinoma, colon cancer, hereditary nonpolyposis colorectal cancer, colorectal adenocarcinomas, gastrointestinal stromal tumors (GISTs), endometrial carcinoma, endometrial stromal sarcomas, esophageal cancer, esophageal squamous cell carcinoma, esophageal adenocarcinoma, ocular melanoma, uveal melanoma, gallbladder carcinomas, gallbladder adenocarcinoma, renal cell carcinoma, clear cell renal cell carcinoma, transitional cell carcinoma, urothelial carcinomas, Wilms tumor, leukemia, acute lymphocytic leukemia (ALL), acute myeloid leukemia (AML), chronic lymphocytic (CLL), chronic myeloid (CML), chronic myelomonocytic (CMML), liver cancer, liver carcinoma, hepatoma, hepatocellular carcinoma, cholangiocarcinoma, hepatoblastoma, Lung cancer, non-small cell lung cancer (NSCLC), mesothelioma, B-cell lymphomas, non-Hodgkin lymphoma, diffuse large B-cell lymphoma, Mantle cell lymphoma, T cell lymphomas, non-Hodgkin lymphoma, precursor T-lymphoblastic lymphoma/leukemia, peripheral T cell lymphomas, multiple myeloma, nasopharyngeal carcinoma (NPC), neuroblastoma, oropharyngeal cancer, oral cavity squamous cell carcinomas, osteosarcoma, ovarian carcinoma, pancreatic cancer, pancreatic ductal adenocarcinoma, pseudopapillary neoplasms, acinar cell carcinomas. Prostate cancer, prostate adenocarcinoma, skin cancer, melanoma, malignant melanoma, cutaneous melanoma, small intestine carcinomas, stomach cancer, gastric carcinoma, gastrointestinal stromal tumor (GIST), uterine cancer, or uterine sarcoma.

Non-limiting examples of other genetic-based diseases, disorders, or conditions that are optionally evaluated using the methods and systems disclosed herein include achondroplasia, alpha-1 antitrypsin deficiency, antiphospholipid syndrome, autism, autosomal dominant polycystic kidney disease, Charcot-Marie-Tooth (CMT), cri du chat, Crohn's disease, cystic fibrosis, Dercum disease, down syndrome, Duane syndrome, Duchenne muscular dystrophy, Factor V Leiden thrombophilia, familial hypercholesterolemia, familial mediterranean fever, fragile X syndrome, Gaucher disease, hemochromatosis, hemophilia, holoprosencephaly, Huntington's disease, Klinefelter syndrome, Marfan syndrome, myotonic dystrophy, neurofibromatosis, Noonan syndrome, osteogenesis imperfecta, Parkinson's disease, phenylketonuria, Poland anomaly, porphyria, progeria, retinitis pigmentosa, severe combined immunodeficiency (scid), sickle cell disease, spinal muscular atrophy, Tay-Sachs, thalassemia, trimethylaminuria, Turner syndrome, velocardiofacial syndrome, WAGR syndrome, Wilson disease, or the like.

C. Customized Therapies and Related Administration

In some embodiments, the methods disclosed herein relate to identifying and administering therapies to patients having a given disease, disorder or condition. Essentially any cancer therapy (e.g., surgical therapy, radiation therapy, chemotherapy, and/or the like) is included as part of these methods. Typically, therapies include at least one immunotherapy (or an immunotherapeutic agent). Immunotherapy refers generally to methods of enhancing an immune response against a given cancer type. In certain embodiments, immunotherapy refers to methods of enhancing a T cell response against a tumor or cancer.

In some embodiments, the immunotherapy or immunotherapeutic agents targets an immune checkpoint molecule.

Certain tumors are able to evade the immune system by co-opting an immune checkpoint pathway. Thus, targeting immune checkpoints has emerged as an effective approach for countering a tumor's ability to evade the immune system and activating anti-tumor immunity against certain cancers. Pardoll, Nature Reviews Cancer, 2012, 12:252-264.

In certain embodiments, the immune checkpoint molecule is an inhibitory molecule that reduces a signal involved in the T cell response to antigen. For example, CTLA4 is expressed on T cells and plays a role in downregulating T cell activation by binding to CD80 (aka B7.1) or CD86 (aka B7.2) on antigen presenting cells. PD-1 is another inhibitory checkpoint molecule that is expressed on T cells. PD-1 limits the activity of T cells in peripheral tissues during an inflammatory response. In addition, the ligand for PD-1 (PD-L1 or PD-L2) is commonly upregulated on the surface of many different tumors, resulting in the downregulation of anti-tumor immune responses in the tumor microenvironment. In certain embodiments, the inhibitory immune checkpoint molecule is CTLA4 or PD-1. In other embodiments, the inhibitory immune checkpoint molecule is a ligand for PD-1, such as PD-L1 or PD-L2. In other embodiments, the inhibitory immune checkpoint molecule is a ligand for CTLA4, such as CD80 or CD86. In other embodiments, the inhibitory immune checkpoint molecule is lymphocyte activation gene 3 (LAG3), killer cell immunoglobulin like receptor (KIR), T cell membrane protein 3 (TIM3), galectin 9 (GAL9), or adenosine Ata receptor (A2aR).

Antagonists that target these immune checkpoint molecules can be used to enhance antigen-specific T cell responses against certain cancers. Accordingly, in certain embodiments, the immunotherapy or immunotherapeutic agent is an antagonist of an inhibitory immune checkpoint molecule. In certain embodiments, the inhibitory immune checkpoint molecule is PD-1. In certain embodiments, the inhibitory immune checkpoint molecule is PD-L1. In certain embodiments, the antagonist of the inhibitory immune checkpoint molecule is an antibody (e.g., a monoclonal antibody). In certain embodiments, the antibody or monoclonal antibody is an anti-CTLA4, anti-PD-1, anti-PD-L1, or anti-PD-L2 antibody. In certain embodiments, the antibody is a monoclonal anti-PD-1 antibody. In some embodiments, the antibody is a monoclonal anti-PD-L1 antibody. In certain embodiments, the monoclonal antibody is a combination of an anti-CTLA4 antibody and an anti-PD-1 antibody, an anti-CTLA4 antibody and an anti-PD-L1 antibody, or an anti-PD-L1 antibody and an anti-PD-1 antibody. In certain embodiments, the anti-PD-1 antibody is one or more of pembrolizumab (Keytruda®) or nivolumab)(Opdivo®. In certain embodiments, the anti-CTLA4 antibody is ipilimumab)(Yervoy®. In certain embodiments, the anti-PD-L1 antibody is one or more of atezolizumab)(Tecentriq®, avelumab)(Bavencio®, or durvalumab) (Imfinzi®.

In certain embodiments, the immunotherapy or immunotherapeutic agent is an antagonist (e.g. antibody) against CD80, CD86, LAG3, KIR, TIM3, GAL9, or A2aR. In other embodiments, the antagonist is a soluble version of the inhibitory immune checkpoint molecule, such as a soluble fusion protein comprising the extracellular domain of the inhibitory immune checkpoint molecule and an Fc domain of an antibody. In certain embodiments, the soluble fusion protein comprises the extracellular domain of CTLA4, PD-1, PD-L1, or PD-L2. In some embodiments, the soluble fusion protein comprises the extracellular domain of CD80, CD86, LAG3, KIR, TIM3, GAL9, or A2aR. In one embodiment, the soluble fusion protein comprises the extracellular domain of PD-L2 or LAG3.

In certain embodiments, the immune checkpoint molecule is a co-stimulatory molecule that amplifies a signal involved in a T cell response to an antigen. For example, CD28 is a co-stimulatory receptor expressed on T cells. When a T cell binds to antigen through its T cell receptor, CD28 binds to CD80 (aka B7.1) or CD86 (aka B7.2) on antigen-presenting cells to amplify T cell receptor signaling and promote T cell activation. Because CD28 binds to the same ligands (CD80 and CD86) as CTLA4, CTLA4 is able to counteract or regulate the co-stimulatory signaling mediated by CD28. In certain embodiments, the immune checkpoint molecule is a co-stimulatory molecule selected from CD28, inducible T cell co-stimulator (ICOS), CD137, OX40, or CD27. In other embodiments, the immune checkpoint molecule is a ligand of a co-stimulatory molecule, including, for example, CD80, CD86, B7RP1, B7-H3, B7-H4, CD137L, OX40L, or CD70.

Agonists that target these co-stimulatory checkpoint molecules can be used to enhance antigen-specific T cell responses against certain cancers. Accordingly, in certain embodiments, the immunotherapy or immunotherapeutic agent is an agonist of a co-stimulatory checkpoint molecule. In certain embodiments, the agonist of the co-stimulatory checkpoint molecule is an agonist antibody and preferably is a monoclonal antibody. In certain embodiments, the agonist antibody or monoclonal antibody is an anti-CD28 antibody. In other embodiments, the agonist antibody or monoclonal antibody is an anti-ICOS, anti-CD137, anti-OX40, or anti-CD27 antibody. In other embodiments, the agonist antibody or monoclonal antibody is an anti-CD80, anti-CD86, anti-B7RP1, anti-B7-H3, anti-B7-H4, anti-CD137L, anti-OX40L, or anti-CD70 antibody.

Therapeutic options for treating specific genetic-based diseases, disorders, or conditions, other than cancer, are generally well-known to those of ordinary skill in the art and will be apparent given the particular disease, disorder, or condition under consideration.

In certain embodiments, the customized therapies described herein are typically administered parenterally (e.g., intravenously or subcutaneously). Pharmaceutical compositions containing the immunotherapeutic agent are typically administered intravenously. Certain therapeutic agents are administered orally. However, customized therapies (e.g., immunotherapeutic agents, etc.) may also be administered by any method known in the art, including, for example, buccal, sublingual, rectal, vaginal, intraurethral, topical, intraocular, intranasal, and/or intraauricular, which administration may include tablets, capsules, granules, aqueous suspensions, gels, sprays, suppositories, salves, ointments, or the like.

EXAMPLES

Example 1: Detecting PPGs

A set of 17,825 clinical samples was processed and analyzed using a 73-gene panel cfDNA test from Guardant Health, Inc. (Redwood City, CA). Among the set, 107 samples were identified as harboring 112 sample-specific PPGs, as shown below in Table 4. This corresponds to a per-sample PPG rate of 0.6%, or one sample-specific PPG per 167 clinical samples.

TABLE 4

| GENE | PPGs | GENE | PPGs |
|------|------|------|------|
| SMAD4 | 49 | CCND1 | 2 |
| GNAS | 19 | HRAS | 2 |
| TP53 | 9 | MET | 2 |
| RAF1 | 5 | MYC | 2 |

TABLE 4-continued

| GENE | PPGs | GENE | PPGs |
|---|---|---|---|
| CDK4 | 4 | NRAS | 2 |
| MAPK1 | 4 | Singletons | 9 |
| STK11 | 3 | | |

In Table 4, all genes for which sample-specific PPGs were detected in at least 1 sample are shown, while all singletons are combined in the "Singleton" category.

Alignment artefacts across the exon-exon junctions created by both germline and somatic sample-specific PPGs may create spurious variant calls, as shown in FIG. 5. The presence of a PPG is revealed both by the presence of multiple soft-clipped reads lacking intronic sequences, as well as discontinuity of coverage at the intron-exon boundary. A spurious A.C SNV call, indicated by the arrow, is observed at 1.7% allele frequency (AF).

Example 2: Clinical Consequence of PPGs

Figure 6:
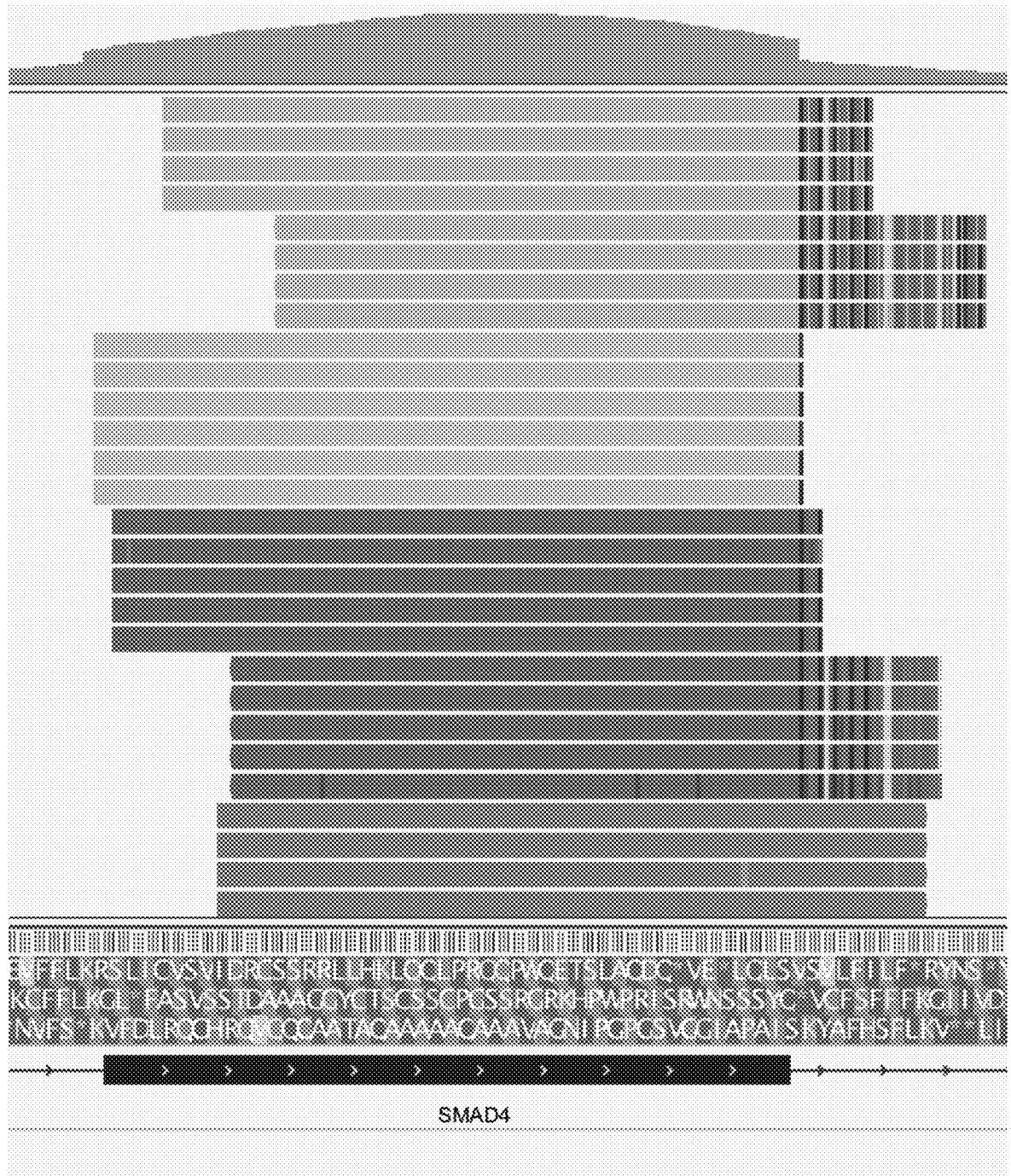
FIG. 6 is a diagram showing mapped sequence reads to SMAD4 exon 11. Reads originating from a single molecule are grouped by color (i.e., greyscale shad) and genomic coordinate in common. The presence of a PPG is revealed both by the presence of multiple soft-clipped reads lacking intronic sequence sequences (multi-colored pattern on the right-hand side of the reads), as well as discontinuity of coverage at the intron-exon boundary (top of the figure). A spurious A>C SNV call, indicated by the arrow, is observed at an allele-frequency of 1.7%.

The presence of PPGs can lead to two different sources of false-positive variant calls. First, alignment artefacts among reads crossing the PPG exon-exon junctions created by PPGs may create spurious variant calls (FIG. 6). Secondly, SNVs present in PPGs may map to the original gene.

Figure 7:
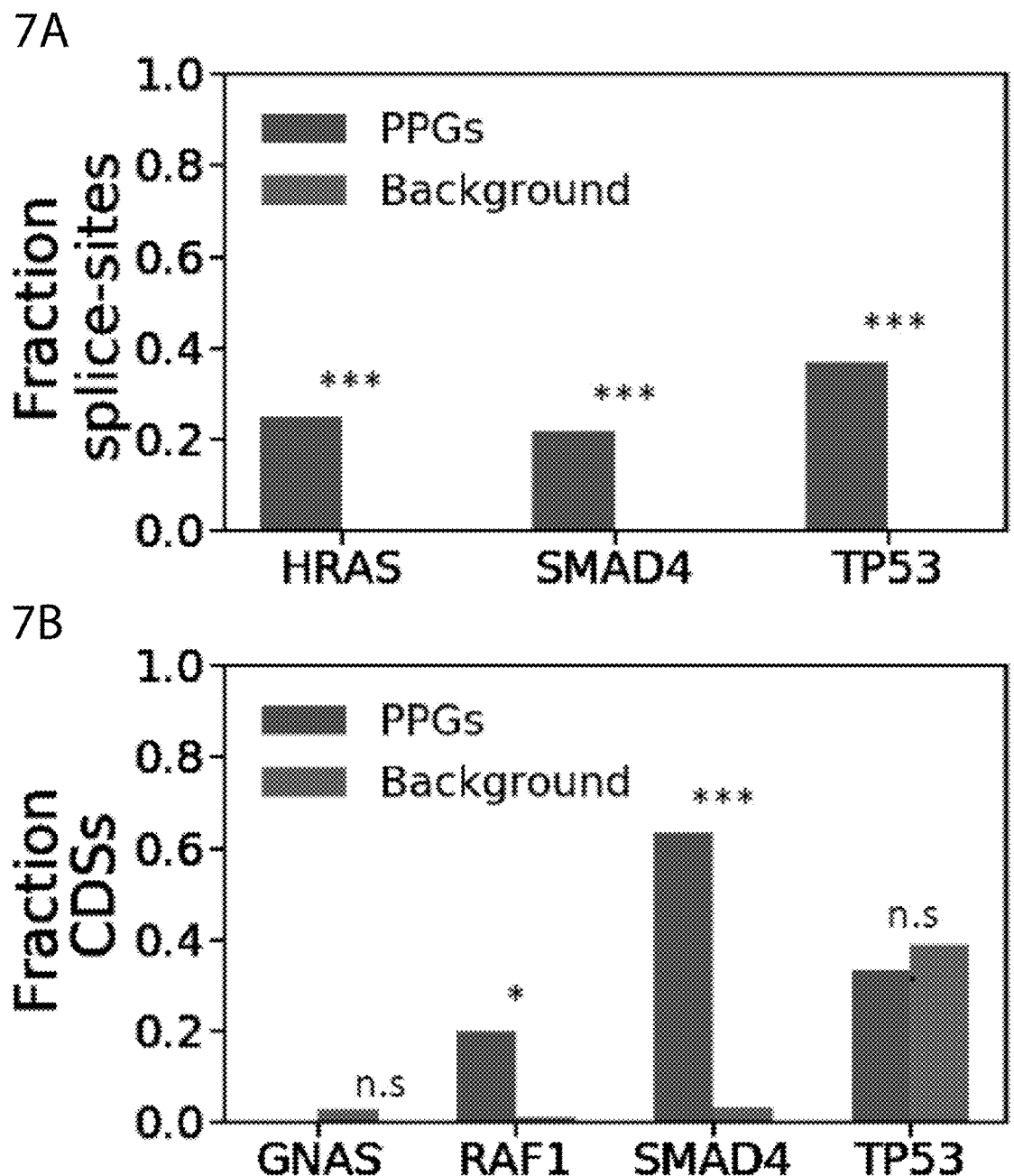
FIG. 7A is a graph showing that when PPGs are detected, SNV calls in splice junctions are observed at higher rates in HRAS, SMAD4, and PT53 than would be expected in non-PPG harboring samples. No SNVs were called within these same junctions in the 10,000 random background samples and as a consequence the grey background bars are at the same height, 0, and therefore not visible.
FIG. 7B is a graph showing that SNVs are called at a higher rate within the coding sequences (CDSs) of SMAD4 and RAF1 when PPGs are detected. All genes with >=PPG harboring samples are shown; neither GNAS nor TP53 displayed a higher rate of CDS SNV calls when PPGs were present. ***, $p<0.01$, *, $p<0.05$; n.s., non-significant based on chi-square test (1 d.f.).

Using a random subset of 10,000 clinical samples in which PPGs were not detected, the presence of PPG copies of several genes was observed to lead to more SNVs than would be expected by chance at intron-exon boundaries (FIG. 7A) and within the coding sequence (CDS) (FIG. 7B).

Example 3: Eliminating False-Positive Variants

In total, 48 SNVs in splice junctions as well as 32 SNVs in CDS were determined to be potentially attributable to the presence of PPGs derived from HRAS, RAF1, SMAD4, and TP53. By performing PPG-aware suppression of false-positive variants, a per-sample false-positive rate increase of 0.45% (80/17,825) was avoided, as shown in Table 5.

TABLE 5

| LOCATION | FALSE-POSITIVES SUPPRESSED | |
|---|---|---|
| | SNVs | PER-SAMPLE RATE |
| Splice junctions | 48 | 0.27% |
| CDS | 32 | 0.18% |

Example 4: Detecting and Suppressing False-Positive Variants Caused by TYRO3 PPGs A set of 2,094 patient samples was processed and analyzed using the a 500-gene panel cfDNA test from Guardant Health, Inc. (Redwood City, CA). Among the set, 1,140 samples were identified as harboring a sample-specific PPGs, for the gene TYRO3. This corresponds to a per-sample PPG rate of 54%, or one PPG per two samples. These samples were assessed for the presence of a suspected false-positive C>T mutation at the TYRO3 locus on chromosome 15 at position 41,862,477 (as known as TYRO3 c.1422C>T).

TABLE 6

| | Samples | TYRO3 c.1422C > T Detected |
|---|---|---|
| PPG Detected | 1,140 | 11 |
| PPG not-detected | 954 | 0 |

In Table 6, the suspected false-positive variant is observed in 11 samples where a PPG is detected, but in no samples where a PPG is not detected, a statistically significant difference (Fisher's Exact Test, $p=0.0013$). As the variant is only seen in the presence of the PPG this suggests that it is an artefact of reads originating from the PPG aligning to the TYRO3 locus.

Figure 8:
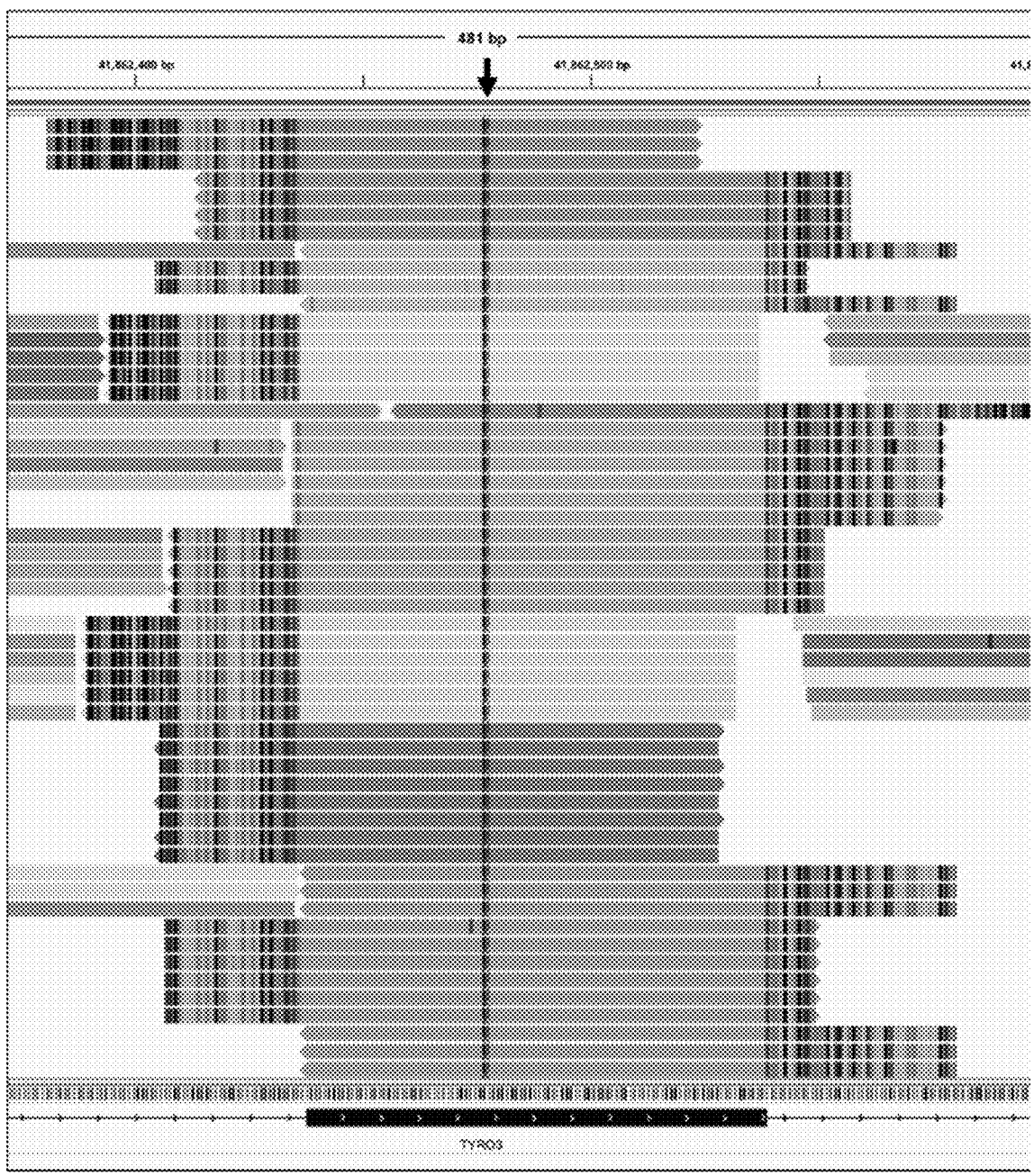
FIG. 8 is a diagram showing mapped sequence reads to TYRO3 on human chromosome 15. Reads originating from a single molecule are grouped by color (i.e., greyscale shade) and genomic coordinates in common. The alignment artefacts across the exon-exon junctions created by PPGs are shown in the context of the TYRO3 locus. A spurious C.T. SNV call (TYRO3 c.1422C>T), is indicated by the arrow

The alignment artefacts across the exon-exon junctions created by PPGs are shown in the context of the TYRO3 locus, as shown in FIG. 8. A spurious C.T. SNV call (TYRO3 c.1422C>T), is indicated by the arrow.

While various embodiments of the disclosure have been shown and described herein, those skilled in the art will understand that such embodiments are provided by way of example only. Numerous variations, changes, and substitutions may occur to those skilled in the art without departing from the disclosure. It should be understood that various alternatives to the embodiments of the disclosure described herein may be employed.

All patent filings, websites, other publications, accession numbers and the like cited above or below are incorporated by reference in their entirety for all purposes to the same extent as if each individual item were specifically and individually indicated to be so incorporated by reference. If different versions of a sequence are associated with an accession number at different times, the version associated with the accession number at the effective filing date of this application is meant. The effective filing date means the earlier of the actual filing date or filing date of a priority application referring to the accession number if applicable. Likewise, if different versions of a publication, website or the like are published at different times, the version most recently published at the effective filing date of the application is meant unless otherwise indicated. Any feature, step, element, embodiment, or aspect of the disclosure can be used in combination with any other unless specifically indicated otherwise. Although the present disclosure has been described in some detail by way of illustration and example for purposes of clarity and understanding, it will be apparent that certain changes and modifications may be practiced within the scope of the appended claims.

What is claimed is:

1. A method for treating a subject having lung cancer, comprising:
   (a) providing a biological sample comprising cell-free nucleic acid molecules from the subject and sequencing the cell-free nucleic acid molecules to generate sequence information comprising genetic sequence reads obtained or derived from the cell-free nucleic acid molecules;
   (b) aligning the genetic sequence reads to a reference sequence to produce aligned sequence reads, wherein the reference sequence is a human genome;
   (c) identifying a set of gene fusion reads that comprise an intragenic fusion breakpoint from the aligned sequence reads;
   (d) detecting an alignment error in a subset of one or more of the gene fusion reads by identifying a potential genetic variant as compared to the reference sequence which: (1) is up to 20 nucleotides adjacent to the intragenic fusion breakpoint, and (2) has a mutant allele fraction that is less than or equal to a mutant allele fraction of the intragenic fusion breakpoint in the biological sample;
   (e) filtering out the alignment error in the subset of the one or more gene fusion reads to produce filtered sequence reads, thereby removing the alignment error and decreasing detection of false positive variants;
   (f) determining filtered sequence reads that include a single nucleotide variant (SNV) or an insertion or deletion (indel) as compared to the reference sequence indicating that the SNV or indel is present in the biological sample of the subject; and
   (g) administering an immunotherapeutic agent to the subject based on the determining of one or more SNVs or indels in (f) to treat the lung cancer, wherein the immunotherapeutic agent is selected from the group consisting of pembrolizumab, nivolumab, ipilimumab, atezolizumab, avelumab, and durvalumab.

2. The method of claim 1, wherein the set of the gene fusion reads corresponds to one or more processed pseudogenes (PPGs).

3. The method of claim 2, wherein the one or more PPGs comprise one or more sample-specific PPGs.

4. The method of claim 3, wherein the one or more sample-specific PPGs identify the subject in a population of subjects.

5. The method of claim 2, wherein the one or more PPGs are derived from the group consisting of: SMAD4, GNAS, TP53, RAF1, CDK4, TYRO3, MAPK1, STK11, CCND1, HRAS, MET, MYC, and NRAS.

6. The method of claim 2, wherein the one or more PPGs comprise two or more PPGs derived from the group consisting of: SMAD4, GNAS, TP53, RAF1, CDK4, TYRO3, MAPK1, STK11, CCND1, HRAS, MET, MYC, and NRAS.

7. The method of claim 2, wherein the one or more PPGs comprise three or more PPGs derived from the group consisting of: SMAD4, GNAS, TP53, RAF1, CDK4, TYRO3, MAPK1, STK11, CCND1, HRAS, MET, MYC, and NRAS.

8. The method of claim 1, wherein the SNV is located at an intron-exon boundary.

9. The method of claim 1, wherein the SNV is located within a gene coding sequence (CDS).

10. The method of claim 1, wherein the biological sample is selected from the group consisting of blood, plasma, serum, urine, saliva, mucosal excretions, sputum, stool, and tears.

11. The method of claim 1, wherein the set of gene fusion reads is identified by aligning and connecting sequenced paired-end reads.

* * * * *

SEQUENCE LISTING

<160> NUMBER OF SEQ ID NOS: 8

<210> SEQ ID NO 1
<211> LENGTH: 45
<212> TYPE: PRT
<213> ORGANISM: Homo sapiens

<400> SEQUENCE: 1

Glu Met Phe Phe Leu Lys Arg Ser Leu Ile Cys Val Ser Val Ile Asp
1               5                   10                  15

Arg Cys Ser Ser Arg Arg Leu Leu His Lys Leu Gln Gln Leu Pro Arg
                20                  25                  30

Gln Gln Pro Trp Gln Glu Thr Ser Leu Ala Gln Asp Gln
            35                  40                  45

<210> SEQ ID NO 2
<211> LENGTH: 12
<212> TYPE: PRT
<213> ORGANISM: Homo sapiens

<400> SEQUENCE: 2

Leu Gln Leu Ser Val Ser Met Leu Phe Ile Leu Phe
1               5                   10

<210> SEQ ID NO 3
<211> LENGTH: 4
<212> TYPE: PRT
<213> ORGANISM: Homo sapiens

<400> SEQUENCE: 3

Arg Tyr Asn Ser
1

<210> SEQ ID NO 4
<211> LENGTH: 8
<212> TYPE: PRT
<213> ORGANISM: Homo sapiens

<400> SEQUENCE: 4

Lys Cys Phe Phe Leu Lys Gly Leu
1               5

<210> SEQ ID NO 5
<211> LENGTH: 44
<212> TYPE: PRT
<213> ORGANISM: Homo sapiens

<400> SEQUENCE: 5

Phe Ala Ser Val Ser Ser Thr Asp Ala Ala Gly Gly Tyr Cys Thr
1               5                   10                  15

Ser Cys Ser Ser Cys Pro Gly Ser Ser Arg Gly Arg Lys His Pro Trp
                20                  25                  30

Pro Arg Ile Ser Arg Trp Asn Ser Ser Ser Tyr Gln
            35                  40

<210> SEQ ID NO 6
<211> LENGTH: 13
<212> TYPE: PRT
<213> ORGANISM: Homo sapiens

<400> SEQUENCE: 6

Val Cys Phe Ser Phe Phe Phe Lys Gly Ile Ile Val Asp
1               5                   10

<210> SEQ ID NO 7
<211> LENGTH: 4
<212> TYPE: PRT
<213> ORGANISM: Homo sapiens

<400> SEQUENCE: 7

```
Asn Val Phe Ser
1

<210> SEQ ID NO 8
<211> LENGTH: 58
<212> TYPE: PRT
<213> ORGANISM: Homo sapiens

<400> SEQUENCE: 8

Lys Val Phe Asp Leu Arg Gln Cys His Arg Gln Val Gln Gln Gln Ala
1               5                   10                  15

Ala Thr Ala Gln Ala Ala Ala Ala Ala Gln Ala Ala Ala Val Ala Gly
            20                  25                  30

Asn Ile Pro Gly Pro Gly Ser Val Gly Gly Ile Ala Pro Ala Ile Ser
        35                  40                  45

Lys Tyr Ala Phe His Ser Phe Leu Lys Val
        50                  55
```